(12) United States Patent
Liu et al.

(10) Patent No.: US 9,427,413 B2
(45) Date of Patent: Aug. 30, 2016

(54) USES OF HYPOXIA-INDUCIBLE FACTOR INHIBITORS

(75) Inventors: Yang Liu, Ann Arbor, MI (US); Yin Wang, Ann Arbor, MI (US); Yan Liu, Ann Arbor, MI (US); Sami N. Malek, Ann Arbor, MI (US); Pan Zheng, Ann Arbor, MI (US)

(73) Assignee: OncoImmune, Inc., Rockville, MD (US)

( * ) Notice: Subject to any disclaimer, the term of this patent is extended or adjusted under 35 U.S.C. 154(b) by 0 days.

(21) Appl. No.: 13/513,659

(22) PCT Filed: Jun. 25, 2010

(86) PCT No.: PCT/US2010/039910
§ 371 (c)(1),
(2), (4) Date: Jul. 2, 2012

(87) PCT Pub. No.: WO2011/068563
PCT Pub. Date: Jun. 9, 2011

(65) Prior Publication Data
US 2012/0264697 A1    Oct. 18, 2012

Related U.S. Application Data

(60) Provisional application No. 61/266,856, filed on Dec. 4, 2009.

(51) Int. Cl.
| | | |
|---|---|---|
| A01N 43/00 | (2006.01) | |
| A61K 31/33 | (2006.01) | |
| A61K 31/00 | (2006.01) | |
| A61K 31/395 | (2006.01) | |
| A61K 31/498 | (2006.01) | |
| A61K 31/565 | (2006.01) | |
| A61K 45/06 | (2006.01) | |

(52) U.S. Cl.
CPC .............. *A61K 31/00* (2013.01); *A61K 31/395* (2013.01); *A61K 31/498* (2013.01); *A61K 31/565* (2013.01); *A61K 45/06* (2013.01)

(58) Field of Classification Search
None
See application file for complete search history.

(56) References Cited

U.S. PATENT DOCUMENTS

| | | |
|---|---|---|
| 6,416,956 B1 | 7/2002 | Berg |
| 2005/0203036 A1* | 9/2005 | Colgan ................. 514/44 |
| 2006/0074030 A1* | 4/2006 | Adams et al. .......... 514/23 |
| 2006/0177451 A1 | 8/2006 | Van Den Oudenrijn et al. |
| 2007/0212360 A1* | 9/2007 | Denko et al. ............ 424/155.1 |
| 2008/0255035 A1* | 10/2008 | Trieu et al. ............ 514/8 |
| 2009/0130091 A1* | 5/2009 | Beachy et al. .......... 424/130.1 |
| 2009/0191225 A1 | 7/2009 | Chang et al. |

FOREIGN PATENT DOCUMENTS

| | | |
|---|---|---|
| WO | 0234291 A2 | 5/2002 |
| WO | 2008016702 A2 | 2/2008 |

OTHER PUBLICATIONS

Cairns et al., "Metabolic Targeting of Hypoxia and HIF1 in Solid Tumors Can Enhance Cytotoxic Chemotherapy," PNAS, May 29, 2007, vol. 104, No. 22, pp. 9445-9450.*
Mehrotra et al., "Cytogenetically Aberrant Cells in the Stem Cell Compartment (CD34+lin−) in Acute Myeloid Leukemia," Blood, vol. 86, No. 3 (1995): pp. 1139-1147.*
Costello et al., "Human Acute Myeloid Leukemia CD34+/CD38− Progenitor Cells Have Decreased Sensitivity to Chemotherapy and Fas-Induced Apoptosis, Reduced Immunogenicity, and Impaired Dendritic Cell Transformation Capacities," Cancer Res 2000; 60:4403-4411.*
Chen et al., "HIF-1 alpha Inhibition Ameliorates Neonatal Brain Damage After Hypoxic-Ischemia Injury," Acta Neurochir Suppl. 2008; 102:395-9.*
Eyler et al., "Survival of the Fittest: Cancer Stem Cells in Therapeutic Resistance and Angiogenesis," Journal of Clinical Oncology, vol. 26, No. 17, Jun. 10, 2008.*
Zhizhong et al., Hypoxia-Inducible Factors Regulate Tumorigenic Capacity of Glioma Stem Cells, Cancer Cell 15, 501-513, Jun. 2, 2009.*
Kong et al., "Echinomycin, a Small Molecule Inhibitor of Hypoxia-Inducible Factor-1 DNA Binding Activity," Cancer Res 2005;65:9047-9055.*
Verenich et al., Mol Pharm, 2010;7(6):2030-9.
Onnis et al., J Cell Mol Med, 2009;13(9A):2780-6.
Schilsky et al., Invest New Drugs, 1991;9(3):269-72 (abstract).
Taylor et al., J Neurooncol, 1993;15(2):181-4 (abstract).
Gradishar et al., Invest New Drugs, 1995;13(2):171-4 (abstract).
Chang et al., Cancer, 1998;82(2):292-300 (abstract).
Muss et al., Am J Clin Oncol, 1990;13(3):191-3 (abstract).
Marshall et al., Invest New Drugs, 1993;11(2-3):207-9 (abstract).
Verenich et al., Therapeutic Promises of 2-Methoxyestradiol and Its Drug Disposition Challenges, Mol Pharm, 2010;7(6):2030-9.
Onnis et al., Development of HIF-1 Inhibitors for Cancer Therapy, J Cell Mol Med, 2009;13(9A):2780-6.
Schilsky et al., Phase II study of echinomycin in patients with advanced breast cancer: a report of cancer and leukemia group B protocol 8641, Invest New Drugs, 1991;9(3):269-72 (abstract).
Taylor et al., Phase II evaluation of echinomycin (NSC-526417) in patients with central nervous system malignancies. A Southwest Oncology Group study, J Neurooncol, 1993;15(2):181-4 (abstract).
Gradishar et al., A phase II clinical trial of echinomycin in metastatic soft tissue sarcoma. An Illinois Cancer Center Study, Invest New Drugs, 1995;13(2):171-4 (abstract).

(Continued)

*Primary Examiner* — Jared D Barsky
(74) *Attorney, Agent, or Firm* — Polsinelli PC; Ron Galant

(57) ABSTRACT

The present invention relates to treating a hematologic cancer using a Hypoxia-Inducible Factor (HIF inhibitor). The invention also relates to inducing acute myeloid leukemia remission using the HIF inhibitor. The invention further relates to inhibiting a maintenance or survival function of a cancer stem cell (CSC) using the HIF inhibitor.

3 Claims, 26 Drawing Sheets

(56) References Cited

OTHER PUBLICATIONS

Chang et al., A randomized phase II trial of echinomycin, trimetrexate, and cisplatin plus etoposide in patients with metastatic nonsmall cell lung carcinoma: an Eastern Cooperative Oncology Group Study, Cancer, 1998;82(2):292-300 (abstract).

Muss et al., Echinomycin (NSC 526417) in squamous-cell carcinoma of the cervix. A phase II trial of the Gynecologic Oncology Group, Am J Clin Oncol, 1990;13(3):191-3 (abstract).

Marshall et al., Phase II trial of echinomycin for the treatment of advanced renal cell carcinoma. A Southwest Oncology Group study. Invest New Drugs, 1993;11(2-3):207-9 (abstract).

Foster, Brenda J., et al.: Echinomycin: The first bifunctional intercalating agent in clinical trials, Investigational New Drugs, Jan. 1, 1986, pp. 403-410: vol. 3.

Kim, Tae-Ue, et al.: Cytotoxic and Apoptotic Effects of Echinomycin on Murine Leukemia Cells, J. Biochem. Mol. Biol., Nov. 30, 1996, pp. 489-492: vol. 29: No. 6.

Chow, Jyh-Ming, et al.: Downregulation of c-Myc determines sensitivity to 2-methoxyestradiol-induced apoptosis in human acute myeloid leukemia, Experimental Hematology, Feb. 1, 2008, pp. 140-148: vol. 36: No. 2.

Panarsky, R., et al., Effectiveness of 17DMAG, a Geldanamycin Derivative, in Murine Acute Myeloid Leukemia, Acta Haematologica, S. Karger, Basel, CH, Jan. 1, 2009, pp. 32-36: vol. 121: No. 1.

Wang, Y., et al., "Echinomycin protects mice against relapsed acute myeloid leukemia without adverse effect on hematopoietic stem cells," Blood, vol. 124, No. 7, pp. 1127-1135 (Aug. 14, 2014).

Lapidot, et al., A cell initiating human acute myeloid leukemia after transplantation into SCID mice, Nature, vol. 367, pp. 645-648 (Feb. 17, 1994).

Lee et al., Human Pancreatic Cancer Stem Cells; Implications for How WE Treat Pancreatic Cancer Translational Oncology, vol. 1, No. 1, Mar. 2008, pp. 14-18.

* cited by examiner a

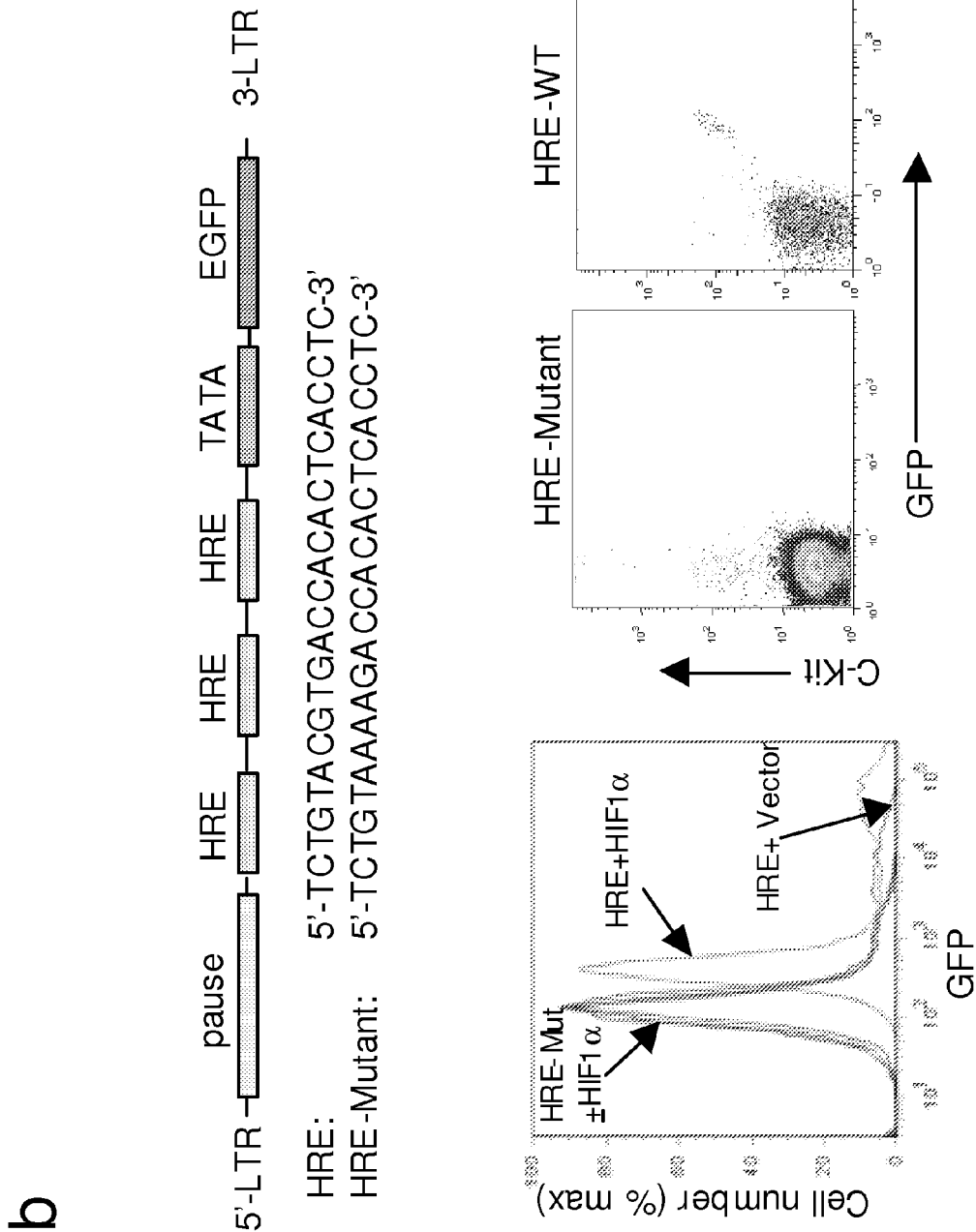

FIGURE 16

```
                        Hes-P-F
Mouse  722  CAAAGCCCAGAGGAAAGAGTTAGCAAAGGGTTAAAATCCTTTTGATTGACGGTTGTAGCCT  781
            ||||||||||||| |||||  ||||||||||||||||||||||||| ||| |||||||||
Human  740  CAAAGCCCAGAGG-GAGAG-TAGCAAAGGGTTAAAATCCTTTTGATTGACGTTGTAGCCT  797
                                            N-box mouse  782  CCGGTGCCCCGGGCTCAGGCGCGGCGCCATTGGCCGCCAGACCTTGTGCCTAGCGGCCAAT  841
            |||||||| ||||||||||||||||||||||||||||||||||||| ||||||||||||
Human  798  CCGGTGCCCTGGGCTCAGGCGCGGCGCCATTGGCCGCCAGACCTTGTGCCTGGCGGCCAAT  857
                           N-box              HRE Mouse  842  GGGGTTCGCAGTCCACGAGCGGGTGCCAGGGTCTCTTCCTCCCATTGGCTGAAAGTTAC  901
            |||||||||||||| ||||||||||||| |||||||||||||||||||||||||||||||
Human  858  GGGGGGCGCCGGTCCACGAGAGCGGTGCCAGGGTCTCCTCCCATTGGCTGAAAGTTAC  917
            CBF1            N-box       HRE Mouse  902  TGTGGGAAAGAAAGTTTGGGAAGTTTCACACGAGCCGTTCGGTGCAGTCCCAGATATAT  961
            ||||||||||||||||||||||||||||||||||| ||||| ||||||||||||||||
Human  918  TGTGGGAAAGAAAGTTTGGGAAGTTTCACACGAGCCGTTCGGTGCAGTCCCAGATATAT  977
                                            TSS Mouse  962  ATAGAGGCCGCCAGGGCCT-GCGGATCACAAGATCTGGAGCTGGTGCTGATAACAGCG  1020
            ||||||||||||||||||| ||||||||| |||||||||||||||||||||||||||
Human  978  ATAGAGGCCGCCAGGGCCTAG-GGATCACAGGATCCGGAGCTGGTGCTGATAACAGCG  1036
                                                    Hes-P-R Mouse  1021 GAATCCCTGTCTACCTCTCCTCCGGTCCTGGAATAGTGCTACGATCACTAAGTAGCC  1080
            |||||||| |||||||||||||| ||||| |||||||||||||||||||||||||||
Human  1037 GAATCCCCGTCTACCTCTCCTCCTGGTCCTGGAACAGCGCTACTGATCACCAAGTAGCC  1096
```

USES OF HYPOXIA-INDUCIBLE FACTOR INHIBITORS

CROSS-REFERENCE TO RELATED APPLICATIONS

This is the national stage of International Application No. PCT/US2010/039910, filed on Jun. 25, 2010, which claims the benefit of U.S. Provisional Patent Application No. 61/266,856, filed on Dec. 4, 2009, the contents of all of which are hereby incorporated herein by reference.

FIELD OF THE INVENTION

The present invention relates to treating hematologic cancers.

BACKGROUND OF THE INVENTION

It is estimated that 12,800 new cases acute myeloid leukemia (AML) will be reported in 2009, with 9000 deaths. Although complete remission can be achieved in most cases through chemotherapy, prolonged remission or cure is rare. Accordingly there is a need in the art to treat AML postremission. Postremission leukemia, however, tends to be more resistant to chemotherapy in general. Underlying reasons for this include expression of the multi-drug resistance protein Pgp1, and possible residence in a bone marrow area that is beyond the reach of drugs.

AML has been hypothesized to be associated with cancer stem cells (CSC). This idea is supported by phenotypically identifiable CSC subsets in AML cells, and the efficacy in testing CSC in an AML model of both in vitro colony-forming units (CFU) and xenogeneic transplantation models.

Many human cancers besides AML contain CSC that are considered to be responsible for driving and maintaining tumor growth and resistance to therapy. Understanding the mechanism of self-renewal of CSC is therefore not only crucial for understanding the fundamental mechanism of cancer development, but also provides new approaches for long-lasting cancer therapy. Much like normal stem cells, self-renewal of CSC involves two related processes. First, the stem cells must undergo proliferation to produce undifferentiated cells. The known pathways for self-renewal of normal and cancer stem cells, including Wnt and Hedgehog, regulate the proliferation, at least in part by controlling the expression of Bmi-1, a critical regulator for proliferation of normal and cancer stem cell proliferation. Second, the CSC must survive in an undifferentiated state throughout tumorigenesis. Survival of CSC may underlie difficulties in treating hematologic cancers, such as AML. Such cancers are particularly more intransigent to therapy postremission. Accordingly, there is a need in the art for additional hematologic cancer therapies that target CSC, including to treat AML. The present invention addresses this need by disclosing a method of treating hematologic cancer using a HIF inhibitor.

SUMMARY OF THE INVENTION

Provided herein is a method for treating a hematologic cancer, which may comprise administering a HIF inhibitor to a mammal in need thereof. The HIF inhibitor may be echinomycin, 2-methoxyestradiol, or geldanamycin. The echinomycin may be administered at a non-toxic dose, which may be 1-100 mcg/m$^2$. The echinomycin may be coadministered with a Hedgehog pathway inhibitor, which may be cyclopamine. The HIF inhibitor may also be coadministered with a second cancer therapy.

The hematologic cancer may be a lymphoma or a leukemia, which may be acute myeloid leukemia. The mammal may carry a cytogenetic alteration, which may be 47,XY,+21;46,XY; 45,XX,−7; 46,XY,t(8;21)(q22;q22); 49,XX,+8,+8,inv(16)(p13.1q22),+21; 46,XX,inv(16)(p13q22)/46,XX; 46,XY,inv(16)(p13q22); 46,XX,t(2;13)(p23;q12)/46,XX; 45,XY,inv(3)(q21q26.2),−7/46,XY; 47,XY,+4,inv(5)(p15q13)/47,s1,−4,+22; 46,XX,t(11;19)(q23;p13.1); 46,XX, t(6;11)(q27;q23)/46,XX; or 46,XX,t(1;17)(p13;q25),t(9;11)(p22;q23). The mammal may carry leukemia cells of the phenotype CD38$^-$CD34$^+$. The patient may carry cancer stem cells, which may be multiple drug resistant, chemoresistant, or radioresistant.

Also provided herein is a method for inducing acute myeloid leukemia remission, which may comprise administering echinomycin to a patient in need thereof. The echinomycin may be administered at a non-toxic dose, which may be 1-100 mcg/m$^2$. Further provided herein is a method for inhibiting a maintenance or survival function of a cancer stem cell (CSC), which may comprise contacting the CSC with a HIF inhibitor.

BRIEF DESCRIPTION OF THE DRAWINGS

FIG. 16. Sequence of mouse and human Hes1 promoter sequence. The N-box is marked in red, CBF1 is marked in blue, TSS is marked in yellow, while the HRE is labeled in green. The primers used for reporter construction and real-time PCR in ChIP assays are marked in pink.

DETAILED DESCRIPTION

Figure 1:
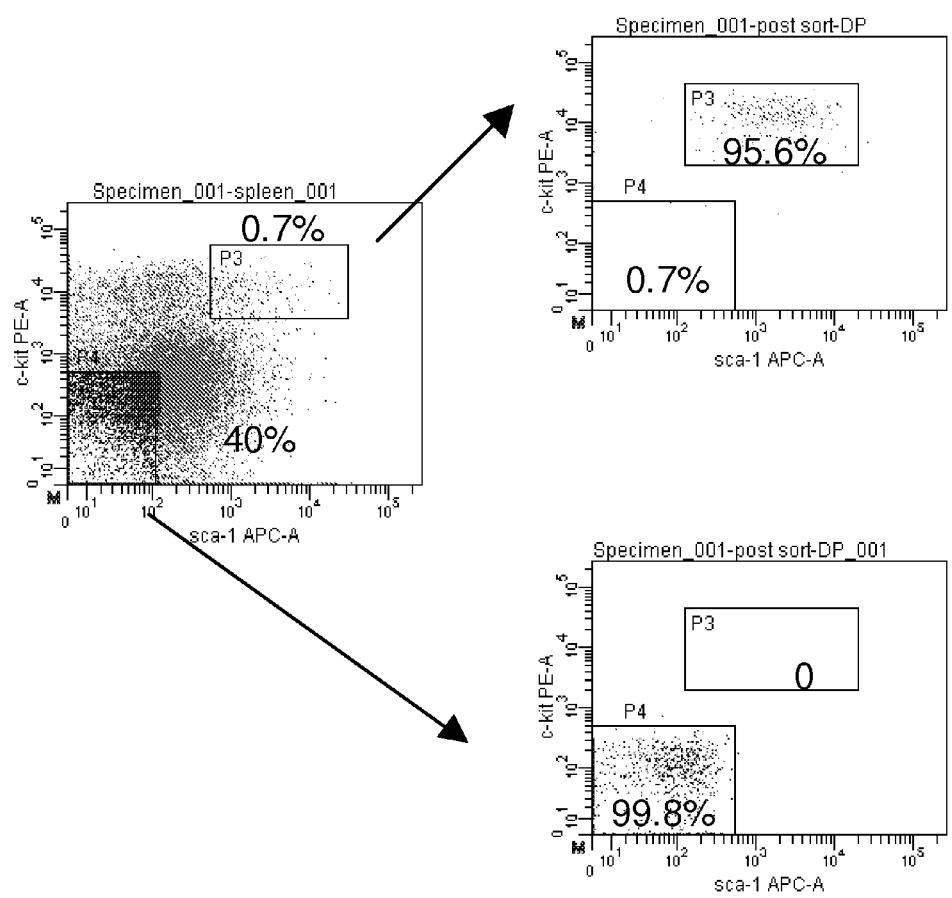
FIG. 1. Isolation of CSC from a spontaneous mouse lymphoma. a. Lymphoma cells, isolated from an enlarged spleen TGB transgenic mice, were sorted by BD FACSAria into c-Kit$^+$Sca-1$^+$ or c-Kit$^-$Sca-1− fractions. The left panel shows tumor phenotype while the right panels show post-sort purities. b. Colony-forming activity of the tumor cells resides within the c-Kit$^+$Sca-1$^+$ subset. The c-Kit$^+$Sca-1$^+$ or c-Kit$^-$Sca-1$^-$ fractions (10$^3$/well) were plated in 1% methylcellulose medium, the colony numbers were counted under a microscope after 7 days of culture. Data shown are means and SD of colony numbers in triplicate plates and are representative of three independent experiments. The insert shows the morphology of a typical colony. c. Photograph of spleens from mice that received either c-Kit$^+$Sca-1$^+$ or c-Kit$^-$Sca-1$^-$ tumor cells. d. Phenotypic conservation and evolution of lymphoma arising from c-Kit$^+$Sca-1$^+$ cells. Lymphoma cells were stained with antibodies against CD8 and Vβ8. The left panel shows cultured lymphoma cells with predominantly high Vβ8$^+$ transgenic CD8$^+$ cells; while the right panel shows lymphoma cells from the spleen of Rag-2$^{-/-}$ mice that received c-Kit$^+$Sca-1$^+$ cells purified from cultured lymphoma cells. Note the increase in Vb8− population. The enlarged double negative populations in the right panel are resident spleen cells.
Figure 1:
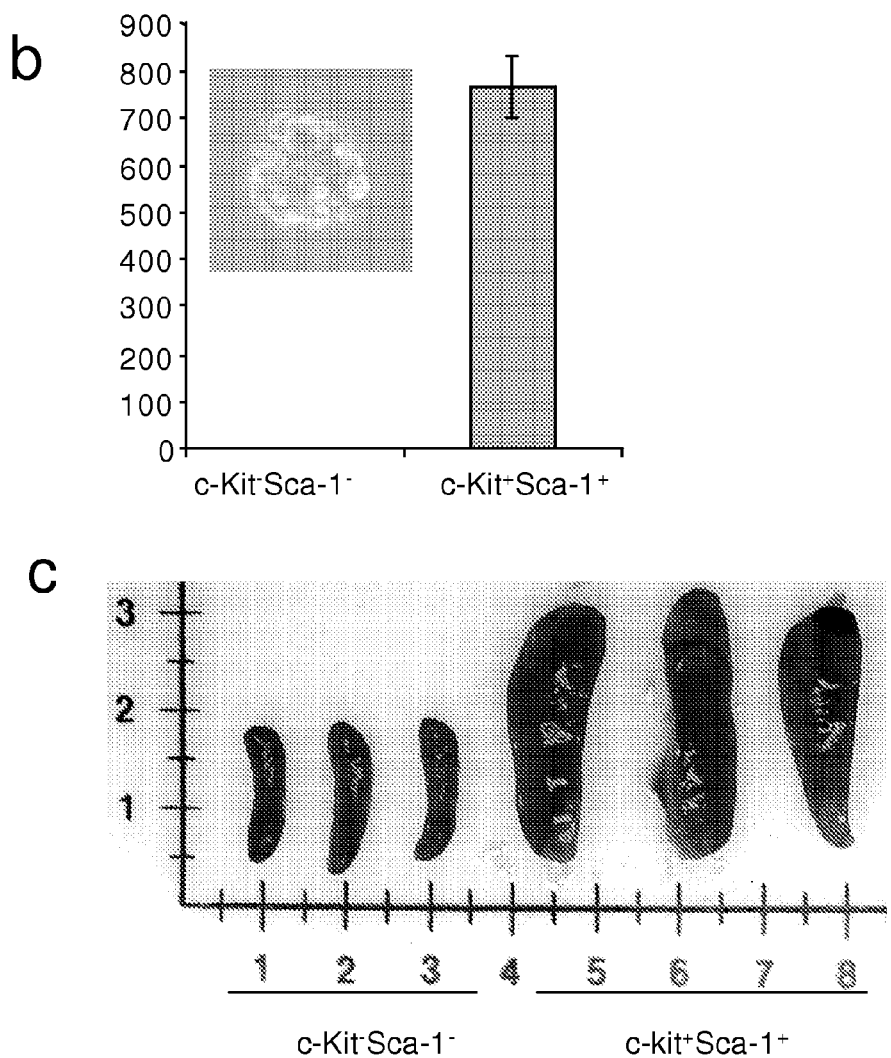
Figure 1:
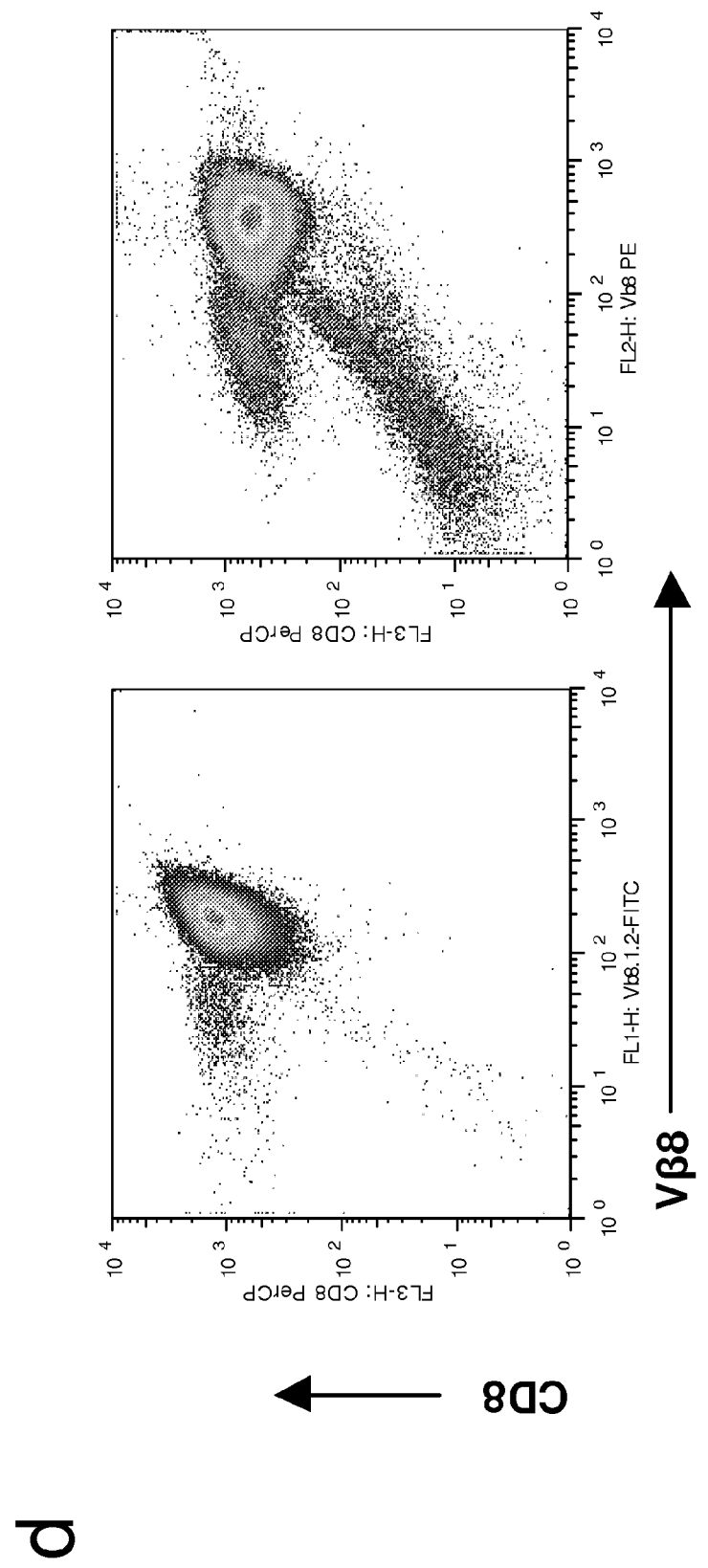

The inventors have made the surprising discovery that the HIF inhibitor echinomycin is capable of treating a hematologic cancer at a non-toxic dose. This indicates a unique susceptibility of lymphoma CSC to echinomycin, and that as little as 30 mcg/m² of echinomycin is sufficient to abrogate lymphoma in 100% of the recipients. For example, in vitro, AML-CFUs of all 6 cases of human AML samples tested were highly susceptible to echinomycin.

Echinomycin was brought into clinical trials about 20 years ago based on its antitumor activity against two i.p. implanted murine tumors, the B16 melanoma and the P388 leukemia. However, testing of the efficacy of echinomycin phase II clinical trials for a number of solid tumors revealed that echinomycin exhibits significant toxicity, and had minimal or no efficacy. The efficacy of echinomycin for treating hematological cancer had not been tested. Additionally, the body-surface adjusted dose used in previous human clinical trials was about 100-fold higher than the dose the inventors have discovered to be effective for treating hematologic cancer. The toxicity observed in previous human trials was likely due to excess dose used, while the lack of effect may have been due to clinical endpoints that do not reflect the unique requirement for HIF in lymphoma CSC. Thus, echinomycin may be used to treat hematologic cancer associated with CSC, including lymphoma, and in particular, at a non-toxic dose.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

A "peptide" or "polypeptide" is a linked sequence of amino acids and may be natural, synthetic, or a modification or combination of natural and synthetic.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

2. Hypoxia-Inducible Factor Inhibitor

Provided herein is an inhibitor of Hypoxia-Inducible Factor protein (HIF). The HIF inhibitor may be echinomycin, 2-methoxyestradiol, or geldanamycin.

a. Echinomycin

The echinomycin may be a peptide antibiotic such as N,N-(2,4,12,15,17,25-hexamethyl-11,24-bis(1-methylethyl)-27-(methylthio)-3,6,10,13,16,19,23,26-octaoxo-9,22-dioxa-28-thia-2,5,12,15,18,25-hexaazabicyclo(12.12.3) nonacosane-7,20-diyl)bis(2-quinoxalinecarboxamide). The echinomycin may be a microbially-derived quinoxaline antibiotic, which may be produced by *Streptomyces echinatus*. The echinomycin may have the following structure.

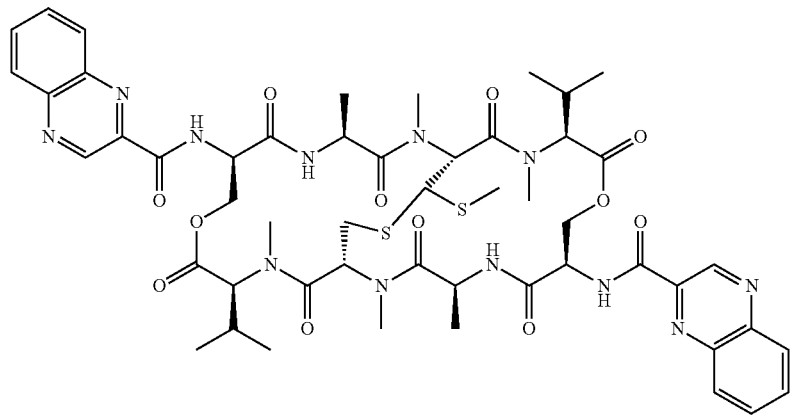 [SMILES: CSC1SC[C@H]2C(=O)N(C)[C@@H](C(C)C)C(=O)OC[C@@H](NC(=O)c3cnc4ccccc4n3)C(=O)N[C@@H](C)C(=O)N(C)[C@@H]1C(=O)N(C)[C@@H](C(C)C)C(=O)OC[C@@H](NC(=O)c1cnc3ccccc3n1)C(=O)N[C@@H](C)C(=O)N2C]

The echinomycin may have a structure as disclosed in U.S. Pat. No. 5,643,871, the contents of which are incorporated herein by reference. The echinomycin may also be an echinomycin derivative, which may comprise a modification as described in Gauvreau et al., Can J Microbiol, 1984; 30(6):730-8; Baily et al., Anticancer Drug Des 1999; 14(3): 291-303; or Park and Kim, Bioorganic & Medicinal Chemistry Letters, 1998; 8(7):731-4, the contents of which are incorporated by reference. The echinomycin may also be a bis-quinoxaline analog of echinomycin b. HIF The HIF may be a functional hypoxia-inducible factor, which may comprise a constitutive b subset and an oxygen-regulated a subunit. The HIF may be over-expressed in a broad range of human cancer types, which may be a breast, prostate, lung, bladder, pancreatic or ovarian cancer. While not being bound by theory, the increased HIF expression may be a direct consequence of hypoxia within a tumor mass. Both genetic and environmental factors may lead to the increased HIF expression even under the normoxia condition. Germline mutation of the von Hippel-Lindau gene (VHL), which may be the tumor suppressor for renal cancer, may prevent degradation HIF under normoxia. It may be possible to maintain constitutively HIF activity under normoxia by either upregulation of HIF and/or down regulation of VHL. The HIF may be HIF1α or HIF2α.

c. Pharmaceutical Composition

Also provided is a pharmaceutical composition comprising the HIF inhibitor. The pharmaceutical composition may be in the form of tablets or lozenges formulated in a conventional manner. For example, tablets and capsules for oral administration may contain conventional excipients may be binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers may be lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants may be potato starch and sodium starch glycollate. Wetting agents may be sodium lauryl sulfate. Tablets may be coated according to methods well known in the art.

The pharmaceutical composition may also be liquid formulations such as aqueous or oily suspensions, solutions, emulsions, syrups, and elixirs. The pharmaceutical composition may also be formulated as a dry product for constitution with water or other suitable vehicle before use. Such liquid preparations may contain additives such as suspending agents, emulsifying agents, nonaqueous vehicles and preservatives. Suspending agents may be sorbitol syrup, methyl cellulose, glucose/sugar syrup, gelatin, hydroxyethylcellulose, carboxymethyl cellulose, aluminum stearate gel, and hydrogenated edible fats. Emulsifying agents may be lecithin, sorbitan monooleate, and acacia. Nonaqueous vehicles may be edible oils, almond oil, fractionated coconut oil, oily esters, propylene glycol, and ethyl alcohol. Preservatives may be methyl or propyl p-hydroxybenzoate and sorbic acid.

The pharmaceutical composition may also be formulated as suppositories, which may contain suppository bases such as cocoa butter or glycerides. The pharmaceutical composition may also be formulated for inhalation, which may be in a form such as a solution, suspension, or emulsion that may be administered as a dry powder or in the form of an aerosol using a propellant, such as dichlorodifluoromethane or trichlorofluoromethane. Agents provided herein may also be formulated as transdermal formulations comprising aqueous or nonaqueous vehicles such as creams, ointments, lotions, pastes, medicated plaster, patch, or membrane.

The pharmaceutical composition may also be formulated for parenteral administration such as by injection, intratumor injection or continuous infusion. Formulations for injection may be in the form of suspensions, solutions, or emulsions in oily or aqueous vehicles, and may contain formulation agents including, but not limited to, suspending, stabilizing, and dispersing agents. The pharmaceutical composition may also be provided in a powder form for reconstitution with a suitable vehicle including, but not limited to, sterile, pyrogen-free water.

The pharmaceutical composition may also be formulated as a depot preparation, which may be administered by implantation or by intramuscular injection. The pharmaceutical composition may be formulated with suitable polymeric or hydrophobic materials (as an emulsion in an acceptable oil, for example), ion exchange resins, or as sparingly soluble derivatives (as a sparingly soluble salt, for example).

(1) Administration

Administration of the pharmaceutical composition may be orally, parenterally, sublingually, transdermally, rectally, transmucosally, topically, via inhalation, via buccal administration, or combinations thereof. Parenteral administration includes, but is not limited to, intravenous, intraarterial, intraperitoneal, subcutaneous, intramuscular, intrathecal, and intraarticular. For veterinary use, the agent may be administered as a suitably acceptable formulation in accordance with normal veterinary practice. The veterinarian can readily determine the dosing regimen and route of administration that is most appropriate for a particular animal. The pharmaceutical composition may be administered to a human patient, cat, dog, large animal, or an avian.

The pharmaceutical composition may be administered simultaneously or metronomically with other treatments. The term "simultaneous" or "simultaneously" as used herein, means that the pharmaceutical composition and other treatment be administered within 48 hours, preferably 24 hours, more preferably 12 hours, yet more preferably 6 hours, and most preferably 3 hours or less, of each other. The term "metronomically" as used herein means the administration of the agent at times different from the other treatment and at a certain frequency relative to repeat administration.

The pharmaceutical composition may be administered at any point prior to another treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins, 8 mins., 7 mins., 6 mins., 5 mins., 4 mins., 3 mins, 2 mins, and 1 mins. The pharmaceutical composition may be administered at any point prior to a second treatment of the pharmaceutical composition including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

The pharmaceutical composition may be administered at any point after another treatment including about 1 min, 2 mins., 3 mins., 4 mins., 5 mins., 6 mins., 7 mins., 8 mins., 9 mins., 10 mins., 15 mins., 20 mins., 25 mins., 30 mins., 35 mins., 40 mins., 45 mins., 50 mins., 55 mins., 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr. The pharmaceutical composition may be administered at any point prior after a pharmaceutical composition treatment of the agent including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

d. Dosage

The pharmaceutical composition may be administered in a therapeutically effective amount of the HIF inhibitor to a mammal in need thereof. The therapeutically effective amount required for use in therapy varies with the nature of the condition being treated, the length of time desired to inhibit HIF activity, and the age/condition of the patient.

The dose may be a non-toxic dose. The dose may also be one at which HIF activity is inhibited, but at which c-Myc activity is unaffected. In general, however, doses employed for adult human treatment typically may be in the range of 1-100 mcg/m$^2$ per day, or at a threshold amount of 1-100 mcg/m$^2$ per day or less, as measured by a body-surface adjusted dose. The desired dose may be conveniently administered in a single dose, or as multiple doses administered at appropriate intervals, for example as two, three, four or more sub-doses per day. Multiple doses may be desired, or required.

The dosage may be a dosage such as about 1 mcg/m$^2$, 2 mcg/m$^2$, 3 mcg/m$^2$, 4 mcg/m$^2$, 5 mcg/m$^2$, 6 mcg/m$^2$, 7 mcg/m$^2$, 8 mcg/m$^2$, 9 mcg/m$^2$, 10 mcg/m$^2$, 15 mcg/m$^2$, 20 mcg/m$^2$, 25 mcg/m$^2$, 30 mcg/m$^2$, 35 mcg/m$^2$, 40 mcg/m$^2$, 45 mcg/m$^2$, 50 mcg/m$^2$, 55 mcg/m$^2$, 60 mcg/m$^2$, 70 mcg/m$^2$, 80 mcg/m$^2$, 90 mcg/m$^2$, 100 mcg/m$^2$, 200 mcg/m$^2$, 300 mcg/m$^2$, 400 mcg/m$^2$, 500 mcg/m$^2$, 600 mcg/m$^2$, 700 mcg/m$^2$, 800 mcg/m$^2$, 900 mcg/m$^2$, 1000 mcg/m$^2$, 1100 mcg/m$^2$, or 1200 mcg/m$^2$, and ranges thereof.

The dosage may also be a dosage less than or equal to about 1 mcg/m$^2$, 2 mcg/m$^2$, 3 mcg/m$^2$, 4 mcg/m$^2$, 5 mcg/m$^2$, 6 mcg/m$^2$, 7 mcg/m$^2$, 8 mcg/m$^2$, 9 mcg/m$^2$, 10 mcg/m$^2$, 15 mcg/m$^2$, 20 mcg/m$^2$, 25 mcg/m$^2$, 30 mcg/m$^2$, 35 mcg/m$^2$, 40 mcg/m$^2$, 45 mcg/m$^2$, 50 mcg/m$^2$, 55 mcg/m$^2$, 60 mcg/m$^2$, 70 mcg/m², 80 mcg/m², 90 mcg/m², 100 mcg/m², 200 mcg/m², 300 mcg/m², 400 mcg/m², 500 mcg/m², 600 mcg/m², 700 mcg/m², 800 mcg/m², 900 mcg/m², 1000 mcg/m², 1100 mcg/m², or 1200 mcg/m², and ranges thereof.

e. Coadministration

The HIF inhibitor may be coadministered with another pharmacological agent. The agent may be an inhibitor of the Hedgehog pathway, which may be cyclopamine. The agent may also be a second cancer therapy. The cancer therapy may be a cytotoxic agent or cytostatic agent. The cytotoxic agent may be selected from the group consisting of: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, and temozolomide; antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxyco-formycin, mitomycin-c, 1-asparaginase, interferons (preferably IFN-γ), etopo side, and teniposide. Other proliferative cytotoxic agents are navelbene, CPT-11, anastrazole, letrazole, capecitabine, reloxafine, cyclophosphamide, ifosamide, and droloxafine.

The cytotoxic agent may be a microtubule affecting agent, which may interfere with cellular mitosis. The microtubule affecting agent may be selected from the group consisting of: allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, (1996) Science, 274:2009) estramustine, nocodazole, and MAP4. The microtubule affecting agent may also be as described in Bulinski (1997) J. Cell Sci. 110:3055 3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; and Panda (1996) J. Biol. Chem 271:29807-29812, the contents of which are incorporated herein by reference.

The cytotoxic agent may also be selected from the group consisting of: epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

The cytostatic agent may be selected from the group consisting of: hormones and steroids (including synthetic analogs): 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, hlorotrianisene, hydroxyprogesterone, aminoglutethimide, estramustine, medroxyprogesteroneacetate, leuprolide, flutamide, toremifene, and zoladex. The cytostatic agent may also be an antiangiogenic such as a matrix metalloproteinase inhibitor or a VEGF inhibitor, which may be an anti-VEGF antibody or small molecule such as ZD6474 or SU6668. The agent may also be an Anti-Her2 antibody from Genentech, an EGFR inhibitor such as EKB-569 (an irreversible inhibitor), or an Imclone antibody C225 immunospecific for the EGFR, or a src inhibitor.

The cytostatic agent may also be selected from the group consisting of: Casodex® (bicalutamide, Astra Zeneca) which renders androgen-dependent carcinomas non-proliferative; the antiestrogen Tamoxifen® which inhibits the proliferation or growth of estrogen dependent breast cancer; and an inhibitor of the transduction of cellular proliferative signals. The inhibitor of the transduction of cellular proliferative signals may be selected from the group consisting of epidermal growth factor inhibitors, Her-2 inhibitors, MEK-1 kinase inhibitors, MAPK kinase inhibitors, PI3 inhibitors, Src kinase inhibitors, and PDGF inhibitors.

3. Method a. Treating a Hematologic Cancer

Provided herein is a method of treating a hematologic cancer. The method may comprise administering a HIF inhibitor to a mammal in need thereof. The mammal may be a human patient. The hematologic cancer may be lymphoma or leukemia. The hematologic cancer may be treated by inhibiting a maintenance or survival function of a CSC. Without being bound by theory inhibiting HIF may target both the cancer stem cell and cancer resistance.

Further without being bound by theory, the CSC in the hematologic cancer may require self-renewal, which may be similar to the requirement in tissue cells. The CSC may require a hypoxic environment, and exposure to a high level of oxygen may reduce CSC function. Self-renewal of CSC function may be strongly inhibited by drugs targeting the HIF pathway. CSC may be addicted to the HIF, which may be associated with over-expression of HIF and down-regulation of VHL. HIF over-expression and VHL down-regulation may be critical in the maintenance of CSC. HIF may work in concert with the Notch pathway to mediate self-renewal of the lymphoma CSC.

(1) Cancer Stem Cell

The cancer stem cell may be chemoresistant or radioresistant. The CSC may also be multiple drug resistant.

(2) Acute Myeloid Leukemia

The leukemia may be acute myeloid leukemia (AML). The AML may be associated with a CSC characterized by the genotype $CD38^-CD34^+$. The AML may also be associated with a patient who carries a cytogenetic alteration. The cytogenetic alteration may be selected from the group consisting of: 47,XY,+21;46,XY; 45,XX,−7; 46,XY,t(8;21)(q22;q22); 49,XX,+8,+8,inv(16)(p13.1q22),+21; 46,XX,inv(16)(p13q22)/46,XX; 46,XY,inv(16)(p13q22); 46,XX,t(2;13)(p23;q12)/46,XX; 45,XY,inv(3)(q21q26.2),−7/46,XY; 47,XY,+4,inv(5)(p15q13)/47,s1,−4,+22; 46,XX,t(11;19)(q23;p13.1); 46,XX,t(6;11)(q27;q23)/46,XX; and 46,XX,t(1;17)(p13;q25),t(9;11)(p22;q23).

The CSC of the AML may be extremely sensitive to the HIF inhibitor. The CFU of AML may be highly susceptible to the HIF inhibitor, with an IC50 between 50-120 pM. The HIF inhibitor may be used to eliminate CSC of AML as part of postremission therapy.

b. Inducing Acute Myeloid Leukemia Remission

Also provided herein is a method for inducing remission of acute myeloid leukemia, which may comprise administering the HIF inhibitor to a mammal in need thereof. The HIF inhibitor may be administered to the mammal during remission of acute myeloid leukemia to prevent future relapse. The HIF inhibitor may be administered as elsewhere disclosed herein.

c. Inhibiting a Maintenance or Survival Function of a CSC

Further provided herein is a method for inhibiting a maintenance or survival function of a CSC. Contacting the CSC with the HIF inhibitor may inhibit the maintenance or survival function. The contacting may comprise administering the HIF inhibitor to a mammal in need of inhibiting the maintenance or survival function of the CSC. The HIF inhibitor may be administered as elsewhere disclosed herein.

The present invention has multiple aspects, illustrated by the following non-limiting examples.

Example 1

Figure 7:
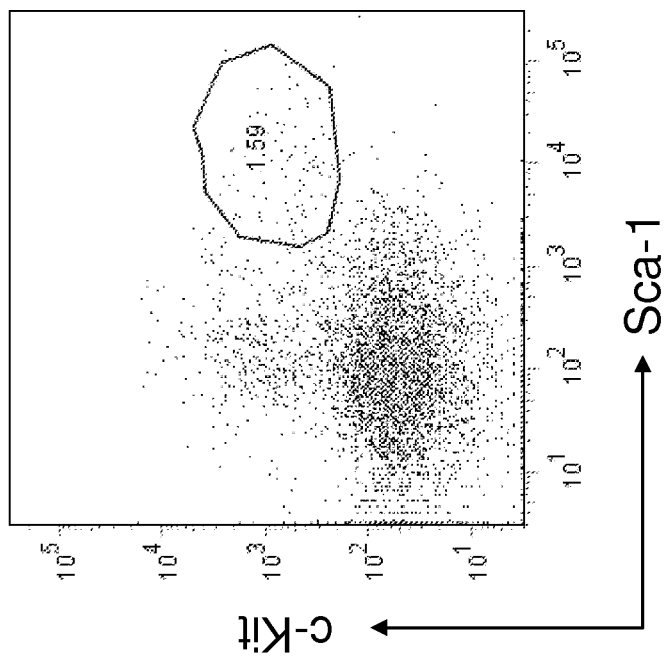
FIG. 7. The progenies of c-Kit+Sca-1+ subset are heterogenous with a small fraction retaining the c-Kit+Sca-1+ phenotype. Ex vivo tumor cells were sorted as described in FIG. 1a and plated in FIG. 1b. Five days later, the cells from the colonies were re-analyzed for expression of c-Kit and Sca-1.

Identification of Self-Renewing Lymphoma Initiating Cells in Syngeneic Immune Competent Host Hundred percent of the transgenic mice (TGB) with insertional mutation of the Epm2a gene succumb to lymphoma. In search for the expression of potential stem cell markers in the TGB lymphoma cells, it was found that a small subset of cells expressed both c-Kit and Sca-1, which partly constitute markers for HSC (FIG. 1a). To test if these cells may have CSC activity, lymphoma cells from the spleen of TGB transgenic mice with tumors were sorted based on expression of both c-Kit and Sca-1 (FIG. 1a right panels). As shown in FIG. 1b, no colony formed from $10^3$ of c-Kit$^-$Sca-1$^-$ cells. In striking contrast, $10^3$ of cells with c-Kit$^+$Sca-1$^+$ yielded about 800 colonies, which suggests that every cells in the subset was CFU. Most colonies are tightly packed (FIG. 1b insert), in contrast to the diverse colonies obtained from bone marrow HSC. The progenies of the c-Kit$^+$Sca-1$^+$ cells consist of both c-Kit$^+$Sca-1$^+$ and c-Kit$^-$Sca-1$^-$ subsets (FIG. 7). Therefore, the c-Kit$^+$Sca-1$^+$ cells are the self-renewing population among the single cells isolated from the TGB lymphoma. To determine if the c-Kit$^+$Sca-1$^+$ cells are also the lymphoma-initiating cells in vivo, we injected either c-Kit$^+$Sca-1$^+$ cells or c-Kit$^-$Sca-1$^-$ cells intraperitoneally (i.p.) into the syngeneic B10BR mice. As shown in Table 1, expt 1, three out of three mice receiving 100 c-Kit$^+$Sca-1$^+$ cells developed lymphomas usually within 10 weeks after injection, yet none of the recipients of $10^4$ of c-Kit-Sca-1– cells did even after 40 weeks of observation. Similar results were obtained when the experiments were repeated by intravenous injection (Table 1, Expt 2). The lymphomas are characterized by enlarged spleens (FIG. 1c), lymph nodes, and metastasis to the liver and lung but not thymus (data not shown), unlike the spontaneously developed lymphoma that first appeared as thymoma and then metastasized into other organ. Furthermore, no constitution of other cell lineages was achieved from the c-Kit$^+$Sca-1$^+$ subset isolated from tumors, which indicates that the c-Kit$^+$Sca-1$^+$ cells are not the tumor-infiltrating HSC. In three rounds of serial transplantation (Table 1, expt 5), the c-Kit$^+$Sca-1$^+$ cells, but not the c-Kit$^-$Sca-1$^-$ cells, gave rise to lymphoma at a comparable potency. The tumors maintained expression of T-cell marker CD8, but gradually lost cell surface expression of the transgenic TCR (FIG. 1d and Table S1). More importantly, the frequency of the c-Kit$^+$Sca-1$^+$ cells remained around 1% (Table S1). Thus, the self-renewing tumor-initiating cells are among the c-Kit$^+$Sca-1$^+$ tumor cells.

TABLE 1

Identification of CSC using c-Kit and Sca-1 markers

| | | | Number of cells injected | | | |
|---|---|---|---|---|---|---|
| Expt | Donor | Recipient | 10,000 | 1,000 | 500 | 100 |
| 1. | c-Kit$^+$Sca-1$^+$ | B10.BR | — | — | 3/3 | 3/3 |
| | c-Kit$^-$Sca-1$^-$ | B10.BR | 0/3 | — | — | — |
| 2. | c-Kit$^+$Sca-1$^+$ | B10.BR | — | — | 4/4 | 3/3 |
| | c-Kit$^-$Sca-1$^-$ | B10.BR | 0/3 | — | 0/3 | — |
| 3. | c-Kit$^+$Sca-1$^+$ | B10.BR | — | — | 5/5 | 5/5 |
| | c-Kit$^-$Sca-1$^-$ | B10.BR | 1/5 | 0/5 | — | — |
| 4. | c-Kit$^+$Sca-1$^+$ | RAG2$^{-/-}$ | — | — | 5/5 | 5/5 |
| | c-Kit$^-$Sca-1$^-$ | RAG2$^{-/-}$ | 1/5 | 0/5 | — | — |
| 5. | Serial transplantation | | | | | |
| | Round 1 | | | | | |
| | c-Kit$^+$Sca-1$^+$ | B10.BR | — | — | 3/3 | 3/3 |
| | c-Kit$^-$Sca-1$^-$ | B10.BR | 1/3 | 0/3 | — | — |
| | Round 2 | | | | | |
| | c-Kit$^+$Sca-1$^+$ | B10.BR | — | — | — | 5/5 |
| | c-Kit$^-$Sca-1$^-$ | B10.BR | 2/5 | — | — | — |
| | Round 3 | | | | | |
| | c-Kit$^+$Sca-1$^+$ | B10.BR | — | — | — | 3/3 |
| | c-Kit$^-$Sca-1$^-$ | B10.BR | 0/3 | (5000/mouse) | — | — |

The donor cells were isolated from either ex vivo lymphoma (expt 1 and 2) or those that have been cultured for more than 30 passages in vitro. The routes of injection were intraperitoneal (i.p.) for experiments 1, 3, and 4, and intravenous for experiment 2. There was no tumor growth (0/3) when 10 c-Kit$^+$Sca-1$^+$ cells were transplanted into B10.BR mice. In experiment 5, donor cells were isolated from ex vivo lymphoma and injected i.p. The lymphoma cells obtained in round 1 were sorted and injected for the second around, then repeated for the third round. The tumor-free mice were observed for 22-40 weeks to confirm the lack of tumor growth.

TABLE S1

Table S1. Conservation and dynamic changes of tumor cell phenotypes.

| | % marker$^+$ cells | | | |
|---|---|---|---|---|
| Markers | Primary | Round 1 | Round 2 | Round 3 |
| c-Kit$^+$Sca-1$^-$ | 3.80 | 3.92 | 4.81 | 1.32 |
| c-Kit$^-$Sca-1$^+$ | 1.52 | 15.38 | 19.5 | 5.14 |
| c-Kit$^+$Sca1$^+$ | 0.87 | 0.81 | 0.97 | 0.83 |
| CD8$^+$Vβ8$^-$ | 3.48 | ND | 47.39 | 54.27 |
| CD8$^+$Vβ8$^+$ | 92.36 | ND | 19.30 | 9.20 |

The c-Kit$^+$Sca-1$^+$ cells from spontaneous tumors were isolated by FACS sorting and serially transplanted into syngeneic B10.BR mice. Single-cell suspensions of tumors that arose in each round were analyzed by flow cytometry using antibodies specific for CD8, Vb8, c-Kit and Sca-1. The % of cells among spleen cells are presented. N.D., not determined.

Using the medium for assaying the colony-forming units (CFU) of hematopoetic progenitor cells, it was possible to establish long term cultures of the TGB lymphoma cells. In over 30 passages, the c-Kit$^+$Sca-1$^+$ cells remained at about 0.5-1.5% of total lymphoma cell population and maintained the CFU in vitro (data not shown) and tumor initiation in vivo (Table 1, expts 3 and 4), with an undiminished efficiency. The fact that the c-Kit+Sca-1$^+$ cells remained at low % indicates that these markers must have been lost during differentiation that occurred after the initiation of the colony formation. The c-Kit+Sca-1− population usually disappeared during in vitro culture. The loss of the Kit+Sca-1− cells during culture does not accompany the loss of tumor-initiation and CFU (data not shown).

Example 2

Essential Role for Up-Regulation of HIF1α Expression in the Maintenance of CSC

Figure 2:
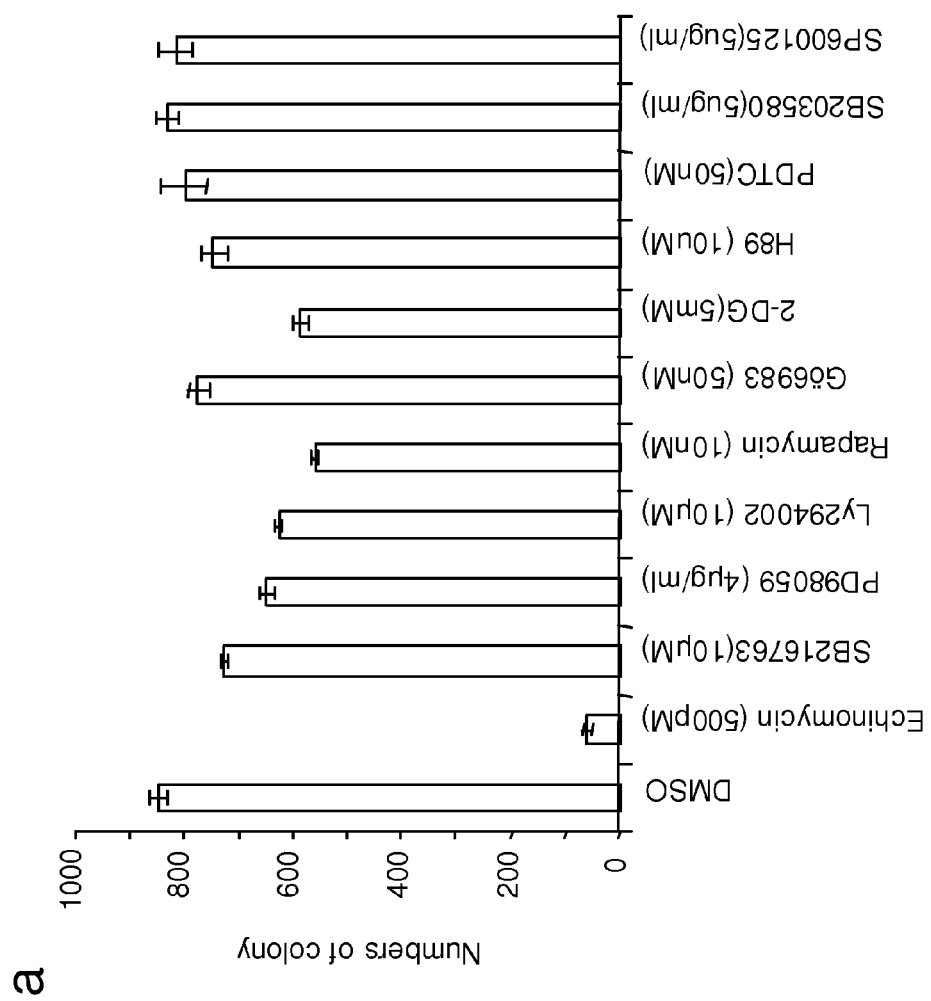
FIG. 2. HIF addiction of CSC. a. Selective ablation of lymphoma CFU by echinomycin. The cultured lymphoma cells were treated with given doses of pharmacologically effective drugs in medium for 24 hours. After washing away the drugs, the cells were cultured in 1% methylcellulose-containing medium, and the colony number was counted after 6 to 7 days. Data shown are means and SD of triplicates and have been confirmed by 3 independent experiments. b. A reporter system for HIF activity in the TGB lymphoma. Diagram of lentiviral construct for HIF activity is shown on the top. Pause, a sequence fragment to eliminate the effect of lentiviral promoter; HRE, Hypoxia response element; TATA, TATA sequence (TATATAAT) (top). Lower left, validation of the reporter. HEK293 cells were transiently transfected with cDNA encoding mutant HIF1α (P402A/P577A) or vector control in conjunction with either HRE-driven EGFP reporter, HER mutant reporter. The cells were analyzed by flow cytometry to detect EGFP expression 36 hours after transduction. Lower right, HIF activity in the lymphoma CSCs as revealed by co-expression of GFP expressing cells and c-Kit in WT HRE, but not mutant HRE lentiviral reporters (lower middle panel). c. IC50 of echinomycin in the inhibition of HIF1α activity in lymphoma CSC. The lymphoma cells transfected with the HRE reporter system were cultured in the presence of different concentration of echinomycin for 12 hours, the % of c-Kit$^+$GFP$^+$ cells was normalized against the untreated group (1.13%, which was defined as 100%). The dose that resulted in 50% reduction of the c-Kit$^+$GFP$^+$ cells is defined as IC50. d. Selectivity of HIF inhibitor for CFU of lymphoma CSC over the CFU from hematopoietic progenitor cells. c-Kit$^+$Sca-1$^+$ cells from either TGB or normal bone marrow were treated with given concentration of echinomycin overnight prior to plating in the medium containing 1% methylcellulose for CFU assay. The data shown were % of untreated controls, and were means+/−S.D. of triplicates. e. Therapeutic effect of a low dose of echinomycin. Cultured lymphoma cells ($1\times10^6$/mouse) were injected i.p. into immune competent B10.BR mice. Fourteen days later, 10 μg/Kg/Injection of echimomycin was injected at a two-day interval for a total of 5 times. Control mice received vehicle only. The mice were observed daily for survival.
Figure 2:
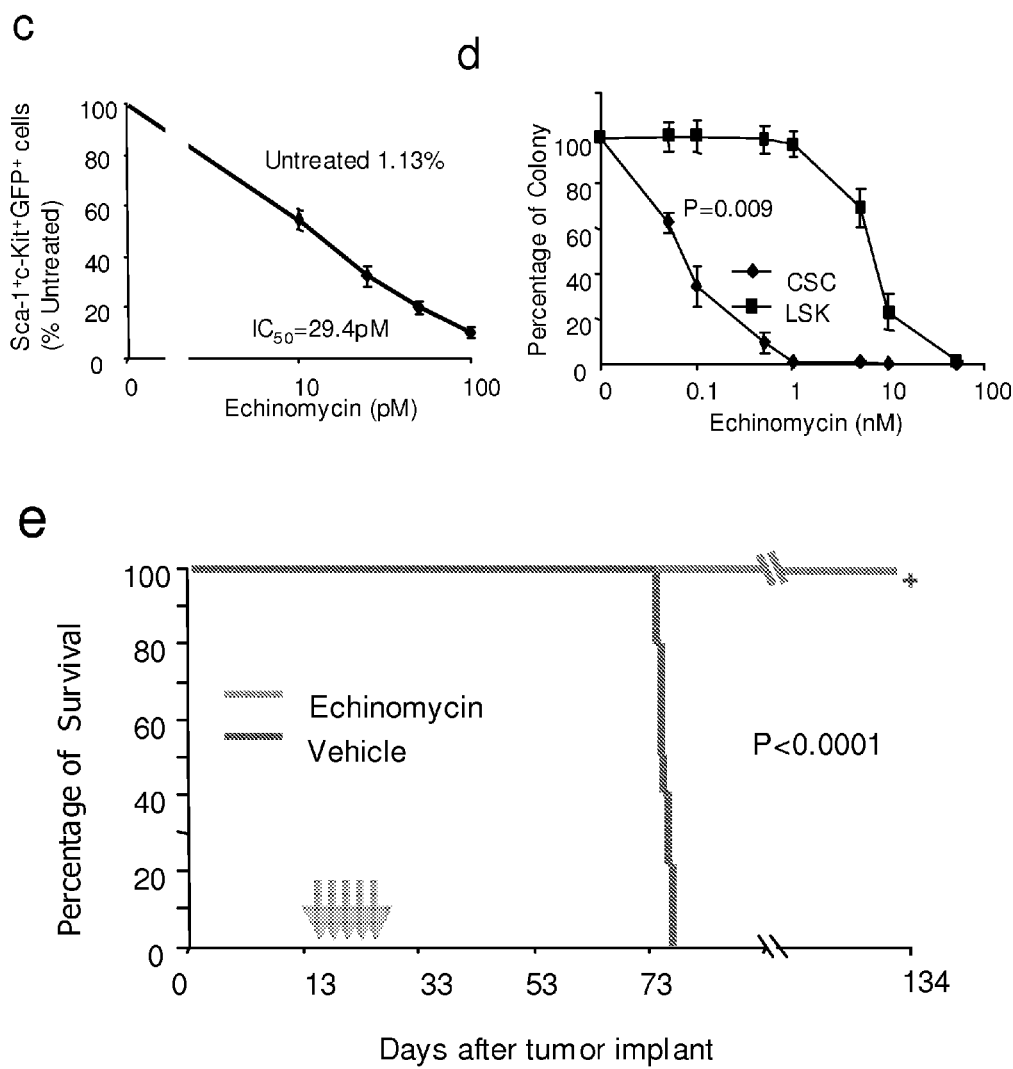

Having established that the c-Kit+Sca-1+ cells are CSCs in the lymphoma model, the molecular program responsible for the self-renewal of CSC activity was identified, using CFU as a surrogate assay. As shown in FIG. 2a, treatment with pharmacologically effective doses of Ly294002 (inhibitor of PI-3 kinase-AKT signal pathway), Rapamycin (mTor-S6K protein synthesis pathway), SB216763 (GSK3β-beta-catenin pathway), Gö6983 (PKC inhibitor), 2-DG (hexokinase inhibitor), H89 (PKA-CREB), PDTC (NF-κB signal pathway), PD98059, SB203580, and SP600126 (MAPK family ERK, p38, and JNK respectively) had no effect on CFU. In contrast, low doses of echinomycin abrogated the CFU.

Figure 8:
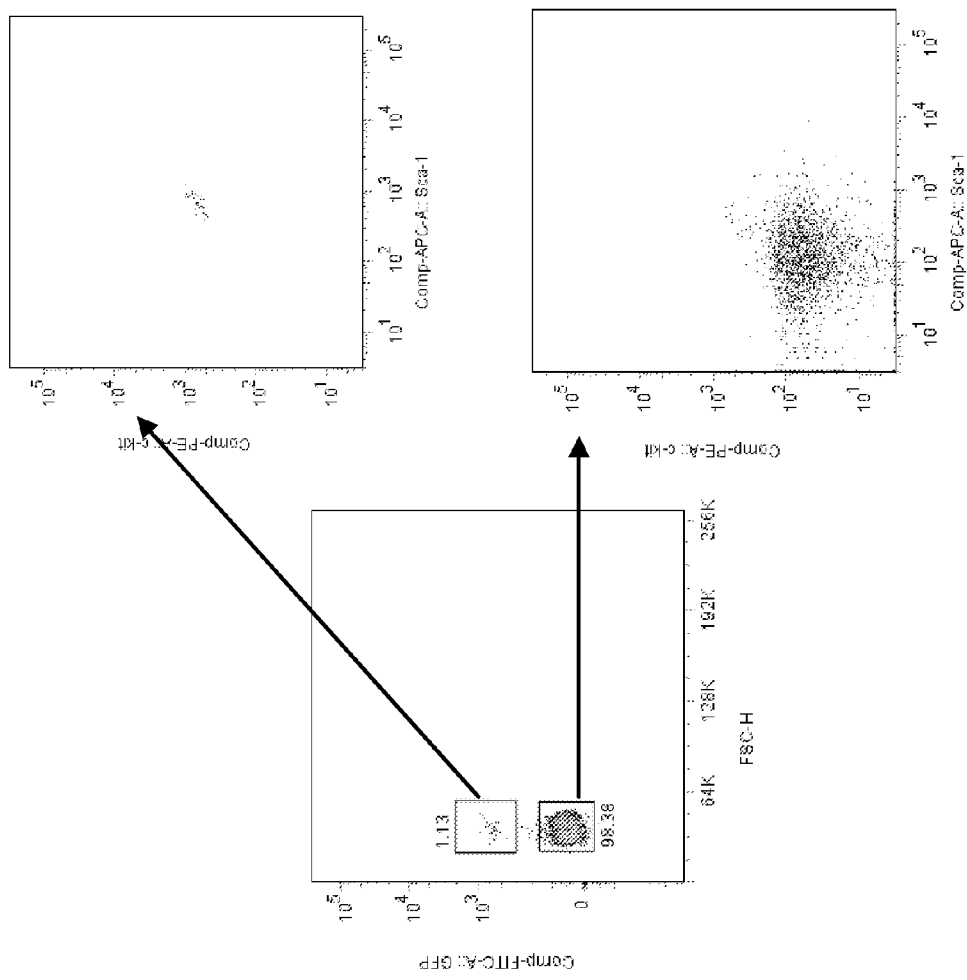
FIG. 8. Cells with HIF activity express both c-Kit and Sca-1. TGB tumor cells were infected with lentiviral vector containing the WT HRE sequence as depicted in FIG. 2d. Three days after infection, the tumor cells were stained with anti-c-Kit and anti-Sca-1 mAbs. The GFP+ and GFP− cells were analyzed for the expression of c-Kit and Sca-1.

In order to monitor the HIF1α activity of the CSC, a lentiviral reporter was generated, consisting of triple HIF1 responsive elements (HRE) in the upstream of a minimum TATA box sequence and an EGFP sequence, as shown in FIG. 2b. A pause sequence was introduced to eliminate effect of LTR promoter on the reporter. To validate the reporter, the HEK293 cells were transiently transfected with either control vector or a mutant HIF1α (P402A/P577A) cDNA in conjunction with either WT or mutant HRE-driven EGFP reporters. The mutation made HIF1α functional under normoxia condition by resisting prolyl hydroxylation-mediated degradation. As expected, the HER-EGFP reporter was specifically induced by HIF1α but not by the control vector. In contrast, the mutant HRE EGFP reporter did not respond to HIF1α (FIG. 2b, lower left panel). Using this lentiviral vector, the effect of echinomycin on the % of cells with active HIF activity was determined. As shown in FIG. 2b lower right panel, a distinct GFP+ population of cells that expressed both c-Kit and Sca-1 markers was found (FIG. 2b and FIG. 8). The expression of GFP reflected HIF activity as it can be abrogated by mutation of the HRE (FIG. 2b, lower middle panel). The sensitivity of this subset to echinomycin was further tested. As shown in FIG. 2c, echinomycin abrogated the CSC with an IC50 of 29.4 pM, which is considerably more sensitive than other cell types, with IC50 in the nM range (Kong et al., 2005).

Figure 9:
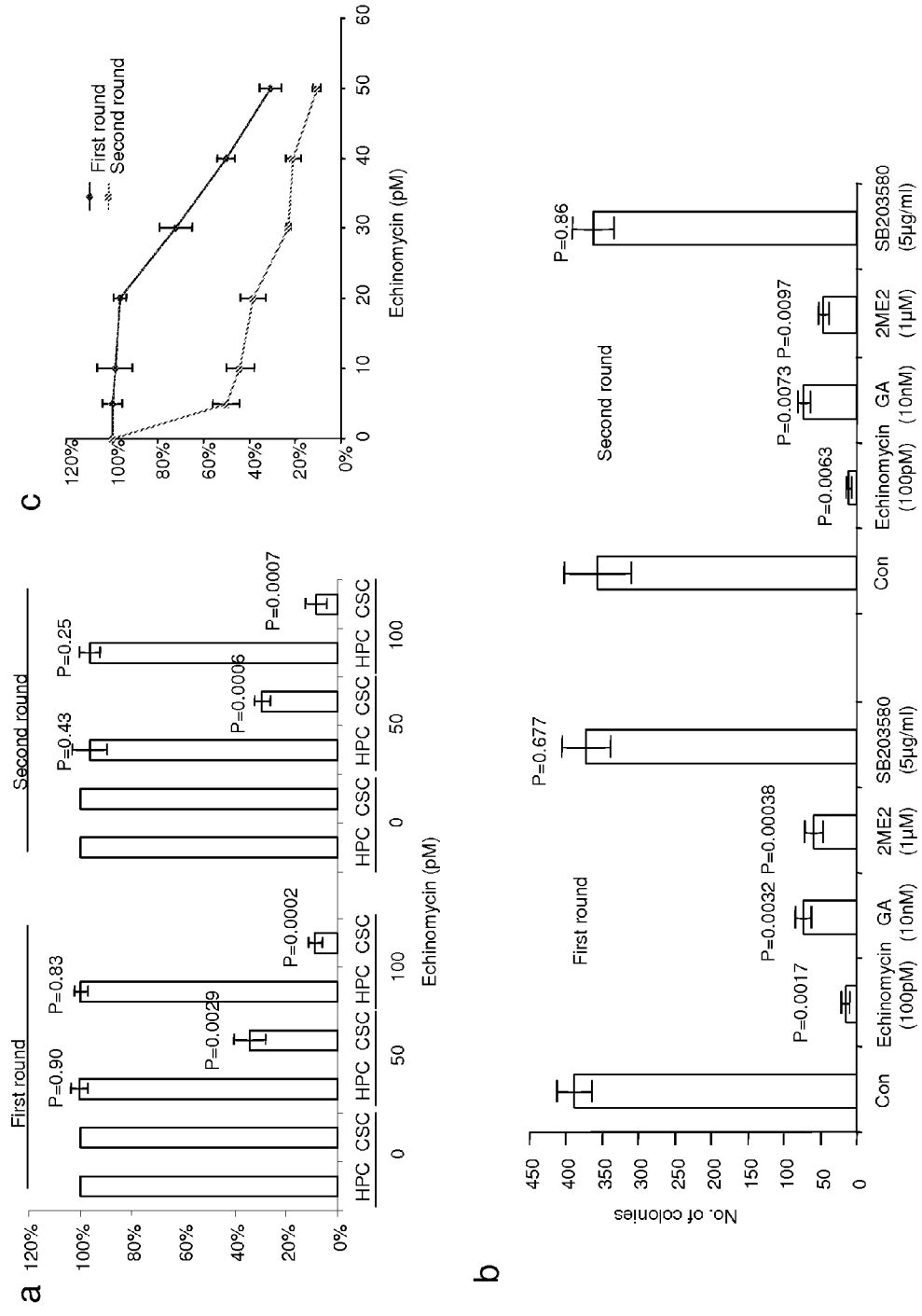
FIG. 9. Inhibition of colony formation of c-Kit+Sca-1+ tumor cells by HIF-1α inhibitors. Data shown were means and S.D. of triplicate culture and have been repeated at least 3 times. a. Continuous inhibition by echinomycin. c-Kit+ Sca-1+ cells sorted from TGB tumor cells were cultured and resorted for c-Kit+Sca-1+ cells. The first and second rounds of sorted cells (1000/well) were cultured in the presence or absence of different doses of echinomycin for 24 hours. The drugs were washed away and the cells plated. The colonies were counted 5 days after culture. b. Inhibition by other classes of HIF1α inhibitors, 2-Methoxyestradiol (2ME2) and Geldanamycin (GA), but not by a P38 inhibitor, SB203580. As described in a, except additional drugs were used as control. c. At low concentrations (5-20 pM), echinomycin inhibits self-renewal of colony-initiating cells without affecting colony formation. Equal aliquots of TGB tumor cells were cultured in methylcellulose-containing medium in the presence of given concentrations of echinomycin for 5 days when the first round colonies were counted. After washing away the drugs, Equal aliquots of cells from the first round were replated. The newly formed colonies were counted. The numbers of colonies were normalized against the untreated group. The numbers of colonies in untreated cultures: first round, 362; second round 202.
Figure 10:
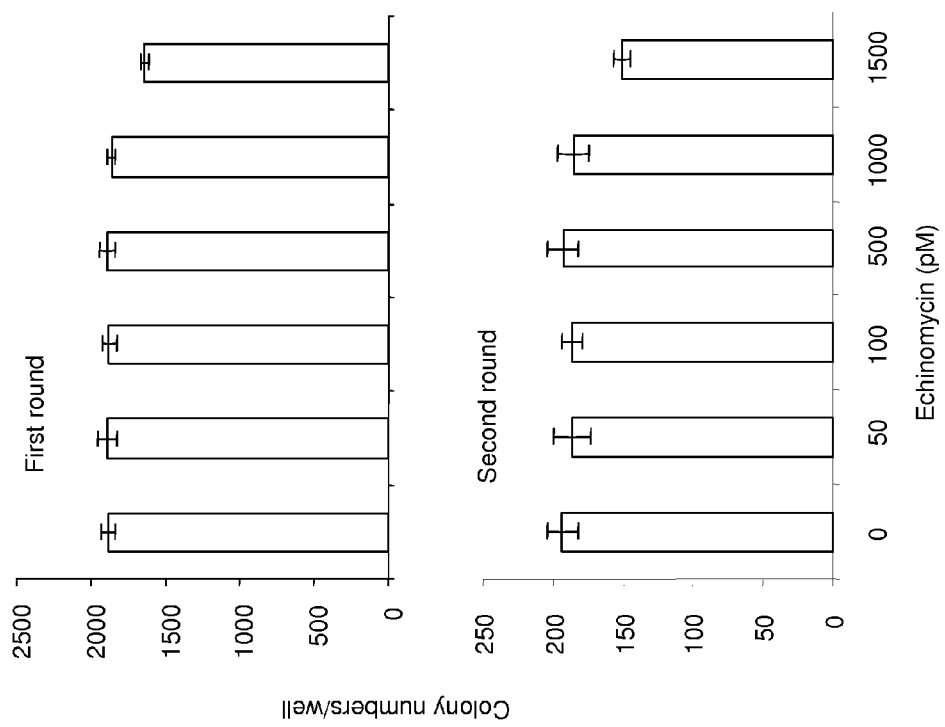
FIG. 10. Continuous resistance of HPC activity to high doses of echinomycin. For the first round, total bone marrow cells (106) were treated with given concentration of echinomycin for 24 hours. After washing away the drugs, aliquots corresponding to $0.25\times10^6$ seeded cells/well were plated into methylcellulose containing medium for CFU assay. The colonies were counted on day 5. For the second round analysis, $0.5\times10^6$ viable cells isolated from the untreated group in the first round were incubated with given concentration of echinomycin. Aliquots corresponding to $5\times10^4$ cells/well were replated and the colonies were counted on day 5. The data shown are means and SD of triplicates.

To substantiate the role of HIF1 activity in CSC function, the effect of HIF inhibitors for both CFU in vitro and tumor-initiating activity in vivo was tested. Since the CFU from the lymphoma CSC and normal hematopoeitic progenitor cells (HPC) can be assayed under similar conditions, the selectivity of echinomycin for HPC vs lymphoma CSC was tested. As shown in FIG. 2d, lymphoma CSC was approximately 100-fold more sensitive to echinomycin than HPC. In serial plating experiments, the effect of echinomycin in both first and second round of CSC was tested. As shown in FIG. 9a, the CSC in both rounds were equally susceptible to echinomycin. The specificity was confirmed by the effect of 3 different classes of HIF1α inhibitors but not by the P38 inhibitor (FIG. S9b). It is worth noting that, at doses (5-20 pM) that had little effect on CFUs in the first round, the CFU in the second-round of colony formation was significantly reduced (FIG. S9c). These data suggest that the in vitro self-renewal of CSC is more addicted to HIF1α than colony initiation. In contrast, neither the first nor the second round of HPC-CFU is affected by considerably higher doses of echinomycin (FIG. 10).

Figure 11:
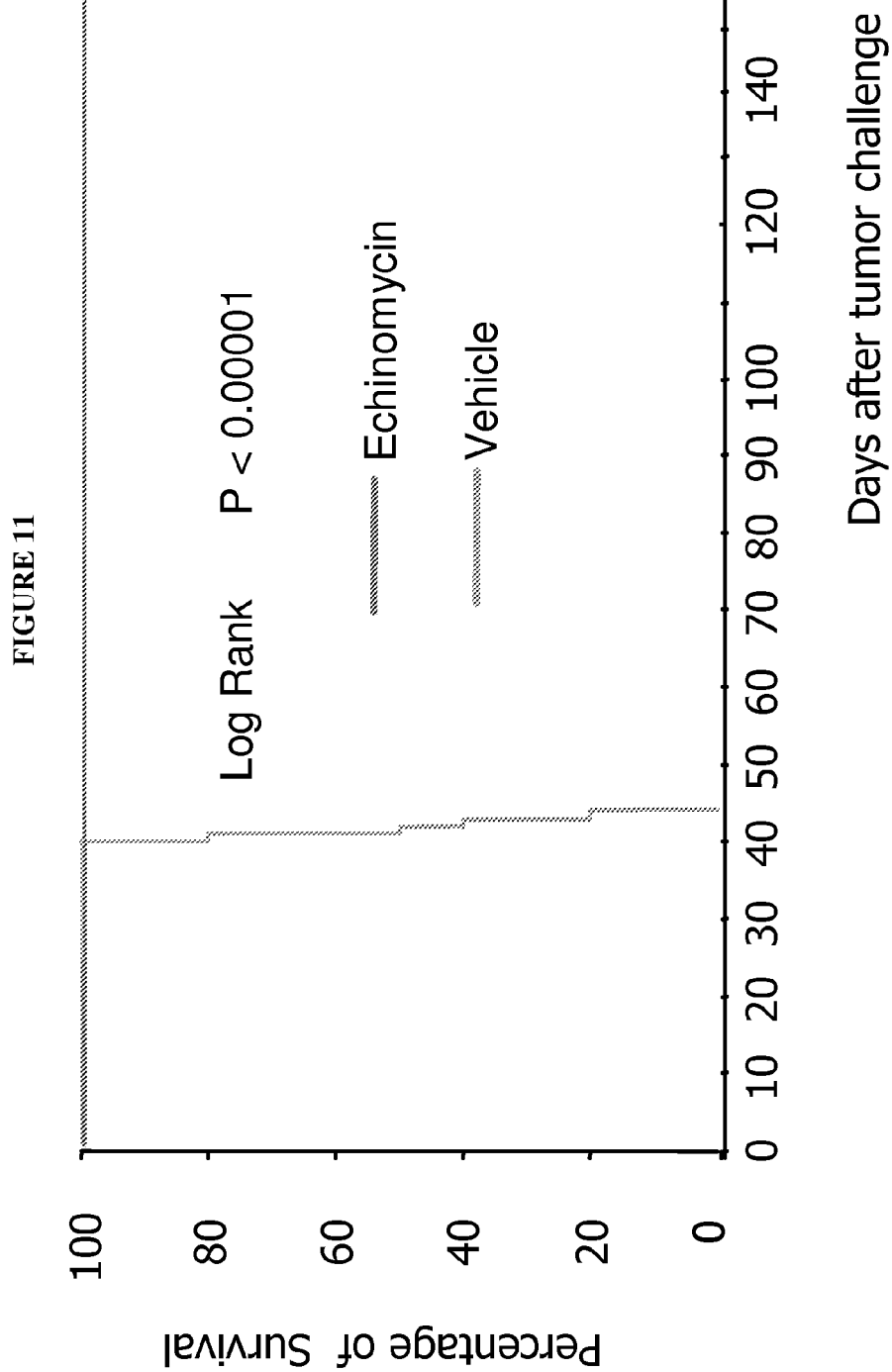
FIG. 11. Therapeutic effect of echinomycin administrated 4 days after tumor transplantation. Cultured lymphoma cells ($1\times10^6$/mouse) were transplanted into immune competent B10.BR mice i.p. Four days later, 10 μg/Kg/Injection of echinomycin was injected with a two day interval for a total of 3 times. Control mice received vehicle only.
Figure 12:
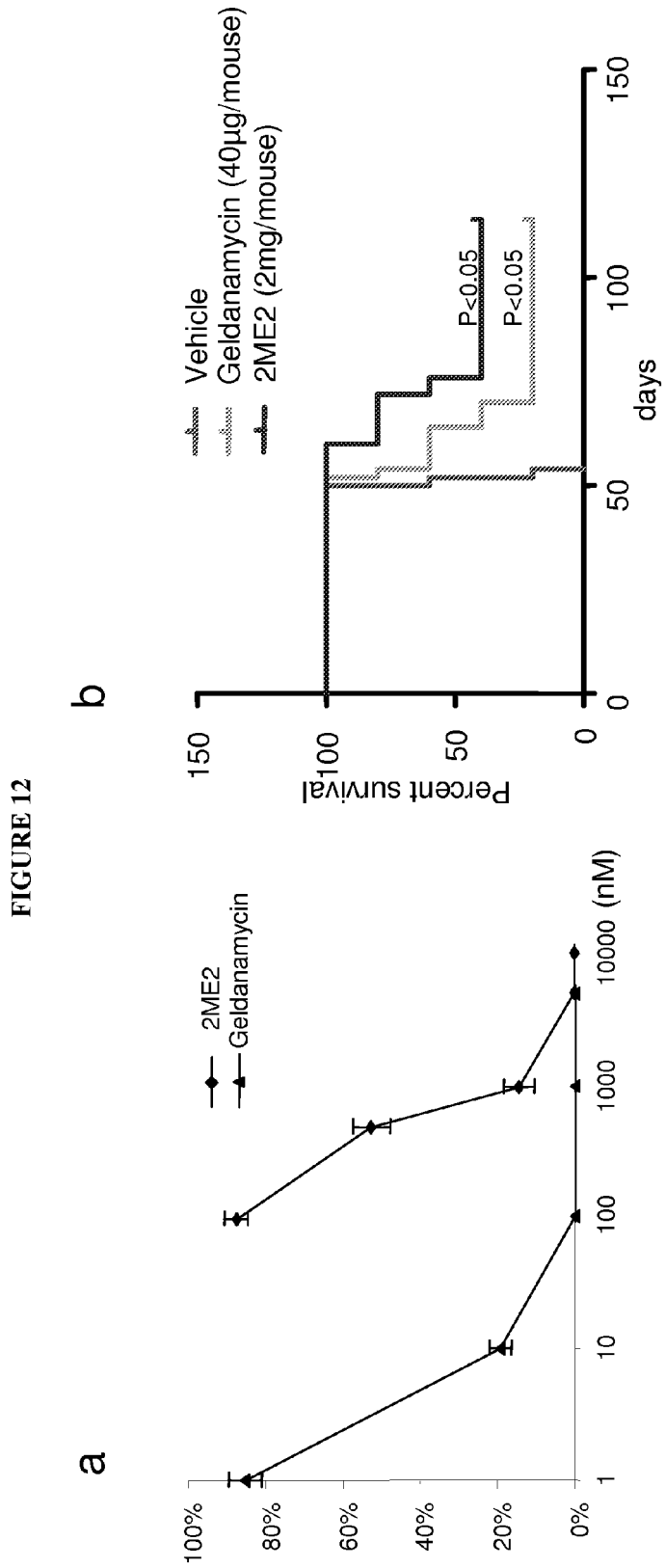
FIG. 12. Multiple HIF-1α inhibitors repress self-renewal and tumor initiating activity of the TGB tumor cells. a. Dose-dependent inhibition of colony formation by 2-methoxyestradiol (2ME2) and Geldanamycin. b. Inhibition of tumor formation by HIF inhibitors 2ME2 and Geldanamycin. Cultured lymphoma cells ($9 \times 10^5$/mouse) were injected into immune competent B10.BR mice i.p. Eight days later, given doses of 2ME2 and Geldanamycin were injected with a two day interval for a total of 5 times. Control mice received vehicle only. The mice were observed daily for survival. The P values given were obtained by log-rank tests in comparison to treated and control groups.

Based on these observations, we explored the therapeutic potential of HIF inhibitors. $1 \times 10^6$ of cultured lymphoma cells were injected i.p. into immune competent B10BR mice. Four or 14 days later, the mice that received lymphoma cells were either treated with vehicle only or 3 (FIG. 11) or 5 (FIG. 2e) injections of 200 ng/mouse of echinomycine at 2 day intervals. As shown in FIG. 2e and FIG. 11, the untreated mice survived only 6-10 weeks, while all treated mice lived until euthanasia at 134 (FIG. 2e) or 252 days (FIG. 11) after tumor cell injection. Two other known HIF inhibitors, 2-methoxyestradiol (Mabjeesh et al., 2003) and Geldanamycin (Minet et al., 1999), also reduced both CFU and tumor initiation of CSC, albeit at less efficacy (FIG. 12). The difference in efficacy may be due to different mechanisms of action and bio-availability. The therapeutic efficacy of these HIF inhibitors demonstrated that HIF may serve as an effective therapeutic target.

Figure 3:
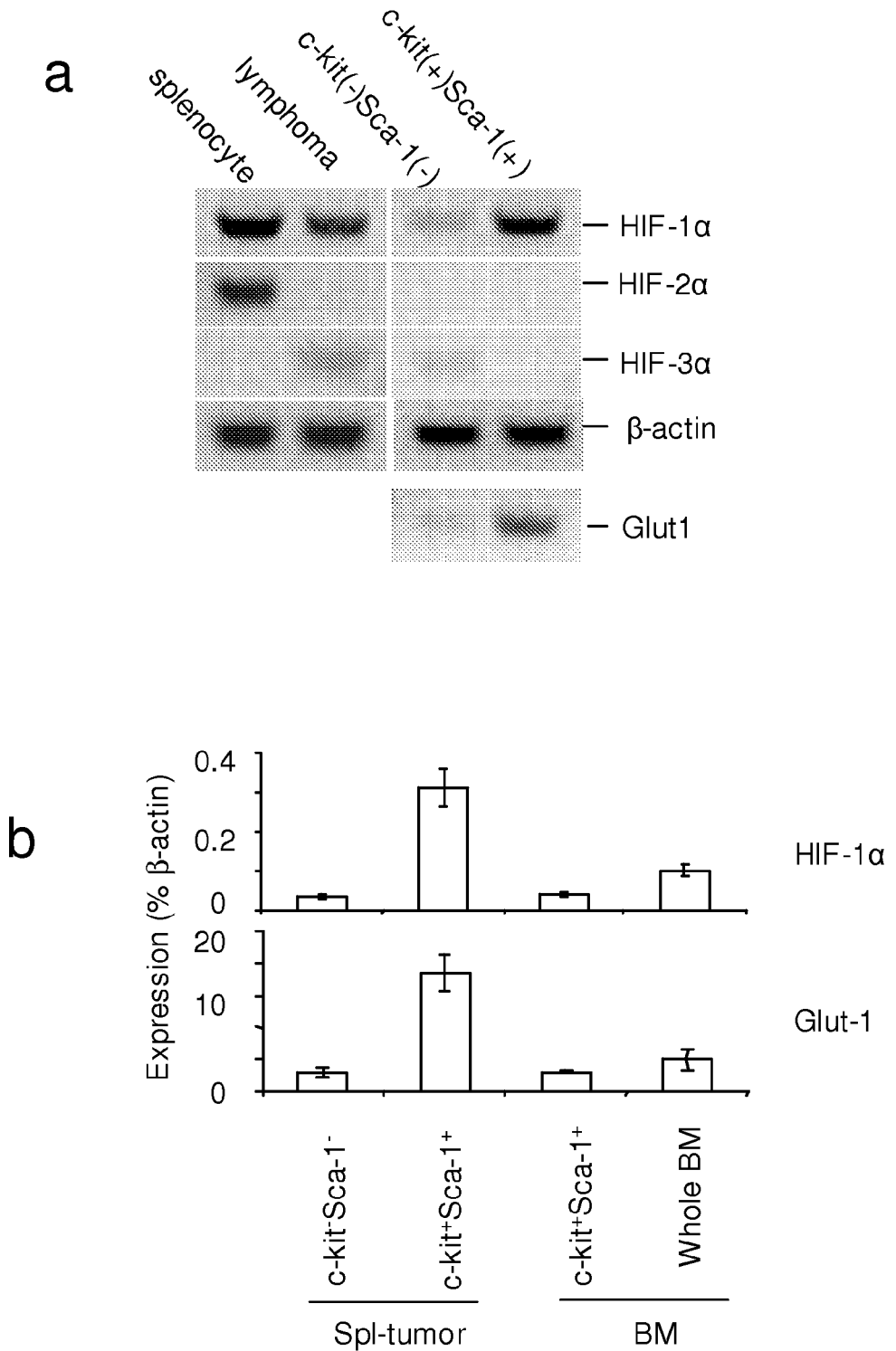
FIG. 3. Increased HIF activity in the lymphoma CSCs under normoxia. a & b. Gene expression. The cultured lymphoma cells were sorted by BD FACSAria sorting system into c-Kit$^+$Sca-1$^+$ or c-Kit$^-$Sca-1$^-$ fractions. The transcripts of HIF1α, HIF-2α, HIF-3α, VHL and Glut1 were determined by RT-PCR. a. Photograph of RT-PCR products. b. Relative expression as measured by real-time PCR: comparison with HPC. Relative expression of HIF1α and VHL transcripts in FACS sorted c-Kit+Sca-1+ cells from either TGB tumor (Spl-tumor) or bone marrow (BM). The expression levels were expressed as fractions of house-keeping gene, b-actin. c. Echinomycin selectively induces apoptosis of CSC. The cultured lymphoma cells were treated with 20 pM echinomycin or vehicle in medium for 16 hours. The treated cells were stained with c-Kit and Sca-1, followed by staining with Annexin V. The stained cells were analyzed by FACS analysis. Data shown are representative of 3 independent experiments. d. Isolation of 4 subsets of tumor cells in AML samples. Bone marrow cells from AML patient MI-AML-36 were stained for CD34 and CD38 and sorted into 4 subsets for RNA isolation. The presort samples and the gates used for sorting are shown in the left panel and the post sorted populations were shown in the middle and right panels. The percentages of cells in each gates are provided in the panels. e. Expression of HIF1α (top) and GLUT1 in the subsets. Data shown are means+/−S.D. of transcript levels of the genes, presented as % of b-actin from the same samples. Enhanced expression in the CD34$^+$CD38$^-$ samples have been observed in all 6 AML samples tested. f. AML-CFU in all 6 AML samples are highly sensitive to echinomycin. AML samples ($2.5\times10^5$/ml) from either peripheral blood (PB) or bone marrow (BM) were pretreated with given concentrations of echinomycin in 2 ml medium for 24 hours. Viable treated cells were then plated at 105/well for CFU assay in triplicates. The colony numbers were counted 7-10 days later. The data shown were % means+/−S.D. of untreated controls.
Figure 3:
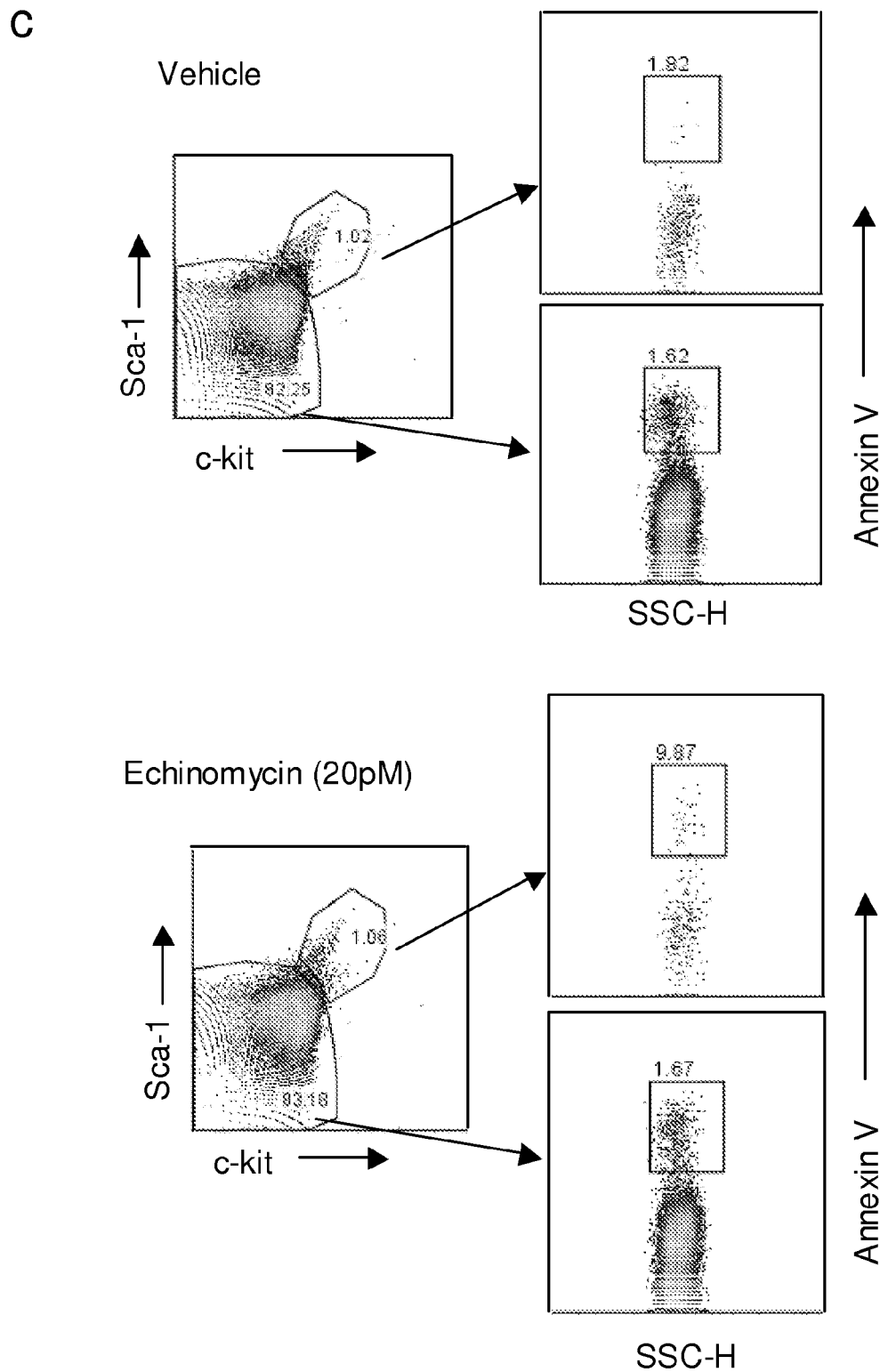
Figure 3:
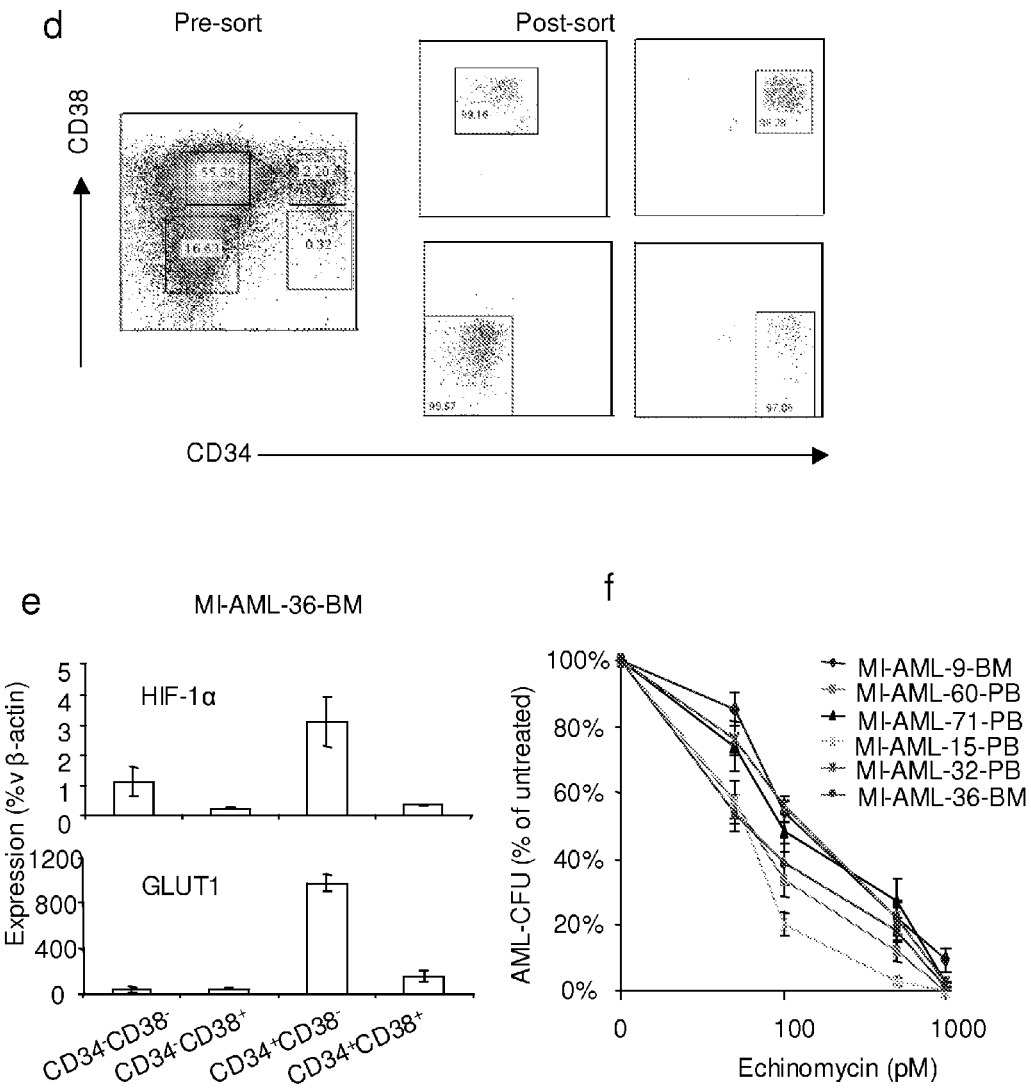

To determine the molecular mechanism for the high HIF1α activity in the CSC, the lymphoma cells were sorted into c-Kit+Sca-1+ or c-Kit−Sca-1− subsets and analyzed HIF1α, HIF-2α and HIF-3α expression by RT-PCR. As illustrated in FIG. 3a and quantified in FIG. 3b, c-Kit+Sca-1+ cells expressed HIF1α at a level that is 4-fold higher than the c-Kit−Sca-1− cells. No expression of HIF2α or HIF3α was detected in the c-Kit+Sca-1+ cells. Consistent with higher levels of HIF1α, expression of glucose transporter Glut1, a known target gene of HIF1α, is also highly elevated in the c-Kit+Sca-1+ cells. In contrast, no up-regulation of HIF1α and Glut1 was observed in the c-Kit+Sca-1+ bone marrow cells. To test if HIF activity is selectively required for survival of the c-Kit+Sca-1+ CSC, the tumor cell culture were treated with low doses of echinomycin (20 pM) for 16 hours and analyzed the % of apoptotic c-Kit+Sca-1+ and c-Kit−Sca-1− tumor cells. In the vehicle treated group, approximately 1.8% of c-Kit+Sca-1+ and c-Kit−Sca-1− tumor cells bound to Annexin V. Echinomycin increased Annexin V+ cells in the c-Kit+Sca-1+ tumor cells by 6-fold, or to about 10%. No effect was observed in the c-Kit−Sca-1− tumor cells (FIG. 3c, lower panel). In three separate experiments involving 10 pM of echinomycin, apoptosis of c-Kit+Sca-1+ tumor cells was on average 3.8+0.8-fold of what was observed in vehicle control. In the same culture, apoptosis of the c-Kit−Sca-1− tumor cells in the echinomycin-treated group is roughly the same (1.2+/−0.3 fold) as the vehicle group. The difference between the two groups is highly significant (P=0.01).

Figure 6:
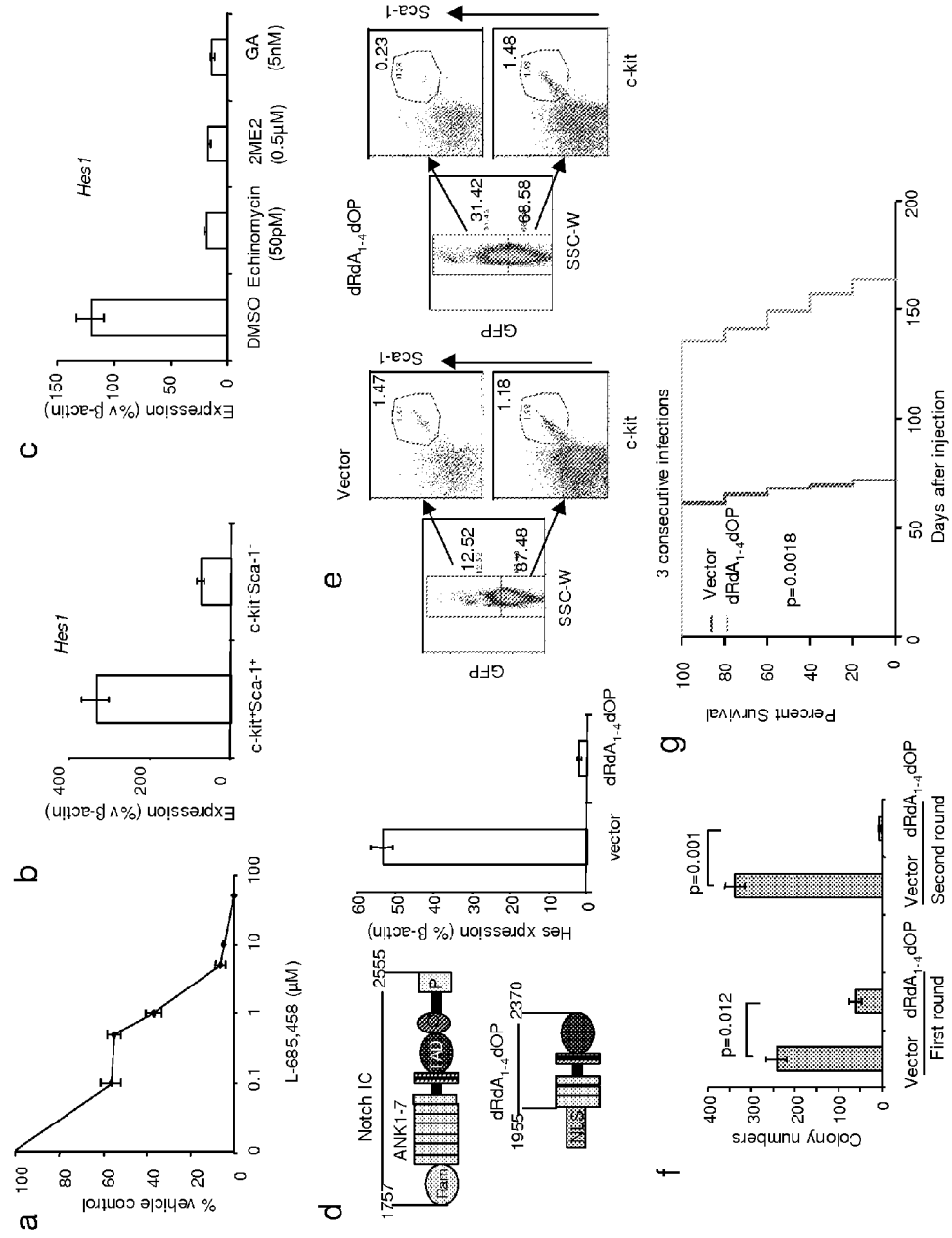
FIG. 6. HIF works in concert with Notch pathway to maintain CSC. a. Inhibition of colony-forming activity of CSC. The cultured lymphoma cells were treated with given doses of L685, 458 for 24 hours. After that, the cells were cultured in 1% methylcellulose-containing medium, and the colony number was counted after 6 to 7 days. Data shown are means+/−SD of triplicate samples and are representative of those of at least 3 independent experiments. b. Enhanced Notch activity in CSC, as indicated by the levels of Hes1 transcripts. The lymphoma cells from spleen with tumor in TGB transgenic mouse were sorted into c-kit$^+$Sca-1$^+$ or c-kit$^-$Sca-1$^-$ fractions. The expressions of Hes1 and mRNA in these two fractions were measured by real time PCR. c. Inhibition of Notch activity by 3 distinct HIF inhibitors. Cultured TGB lymphoma cells were stained with APC conjugated anti-c-Kit-antibody and enriched twice using anti-APC coated MACS beads according to manufacturer's protocol (Militenyi Biotec). The c-kit positive cells-enriched samples (60.4% c-Kit+ cells) were treated with inhibitors of HIF for 16 hours. The mRNA from the treated cells were extracted for quantitation by real-time PCR. Data shown are means+/−SD of triplicates and represent those from at least 3 independent experiments. 2ME2, 2-methoxyestradiol; GA, geldamycin. d-g. A critical role for Notch in maintenance of CSC, as revealed by ectopic expression of Notch I-C dRdA$_{1-4}$2dOP. d. A truncated Notch gene with potent dominant negative activity in inhibiting the expression of Notch target gene Hes. The upper left panel shows the diagram of the intracellular portion of Notch protein, with the position of RAM, 7 ankyrin repeats (ANK1-7), transcriptional activation domain (TAD), C-terminal OPA (O) and PEST (P) sequence are marked. The lower left panel showed the composition of the dRdA$_{1-4}$dOP mutant lacking RAM, ANK1-4 and C-terminal O and P sequence, but with insertion of nuclear localization sequence (NLS). The right panel show dominant inhibition of Hes expression. After three consecutive transductions by either vector control or the dRdA$_{1-4}$dOP mutant, the RNA were isolated and the transcripts of Hes measured by quantitative PCR. Data shown are means of triplicates and have been reproduced by two independent experiments. e. Notch I-C deltaRAM abrogates the c-Kit+Sca-1+ subset. TGB tumor cells were infected with either lentiviral vector control, or lentiviral vector expressing dRdA$_{1-4}$dOP. Three days after infection, the bulk tumor cells were analyzed by flow cytometry. The GFPhi and GFPlo cells were gated and analyzed for expression of c-Kit and Sca-1. f. Notch IC-dRdA$_{1-4}$2dOP reduces in vitro self-renewal activity of CSC. The cultured lymphoma cells were infected with either lentiviral vector encoding dRdA$_{1-4}$dOP or vector control by spinoculation. The same numbers of infected cells were seeded into 1% of methylcellulose culture medium for 3 days and the numbers of colony with GFP were counted under microscope. The same procedure was performed for second round colony formation assay. Data shown are the means and SD of the colony numbers in triplicate plates, and are representative of those from at least three independent experiments. g. dRdA$_{1-4}$dOP abrogates tumor-initiating activity. TGB tumor cells were infected 3 times with lentiviral expressing vector alone or HIF1α ShRNA and then injected into B10.BR mice ($1\times10^6$/mouse, i.p.). The survival of the recipient mice was compared by Kaplan-Meier analysis with statistical significance determined by log-rank tests. All succumbed mice have developed lymphoma as revealed by necropsy. This experiment has been repeated twice. h-l. HIF1α inhibits negative feedback regulation of Hes1 by preventing Hes1 binding to the N-boxes in the Hes1 promoter. h. Diagram of Hes1 promoter. Detail sequence is provided in FIG. 16. i. HIF1α did not co-operate with Notch directly in activating Hes1 promoter. The Hes1 promoter sequence (−225 to +65, TSS as +1) were linked to GFP and transfected into 293 cells in conjunction with vector controls, or vector containing cDNA encoding HIF1α (P402, 577>A, called HIF1α-PA), Notch-IC cDNA or Notch-IC+HIF1αPA. The promoter activity is measured by the green fluorescence intensity of transfected cells. Data shown were relative intensities. The intensity of Hes1-GFP reporter is defined as 1.0. Transfection efficiency is normalized by co-transfected Renilla luciferase. j. HIF1α partially inhibited Hes1-mediated repression of the Hes1 promoter. As in i, except that the Hes1 or mutant HIF1α cDNA are used. k. HIF1α diminishes the negative auto-regulation of Hes1 expression in Notch signaling. As in i, except different combination of cDNAs were used. Activity of Hes1 reporter in the absence of transfected Hes, HIF1α-PA and Notch is defined as 1.0. l. Competitive inhibition between HIF1α-PA and Hes1 to Hes promoter, as revealed by chIP. cDNAs encoding Flag or Myc-tagged Hes1 and HIF-1αPA were transfected into 293 cells. Thirty-six hours after transfection, the transfectants were subject or ChIP. Equal fractions of cells in each group were used for Western blot to confirm essentially identical levels of protein expression when Hes1 and HIF1α-PA were transfected alone or in combination (data not shown). The data present are means+/−S.D. (n=3) of % of input DNA, as measured by real-time PCR using primers marked in FIG. 16. Data shown in i-1 are means+/−S.D. of triplicates. The experiments have been repeated at least 3 times.
Figure 6:
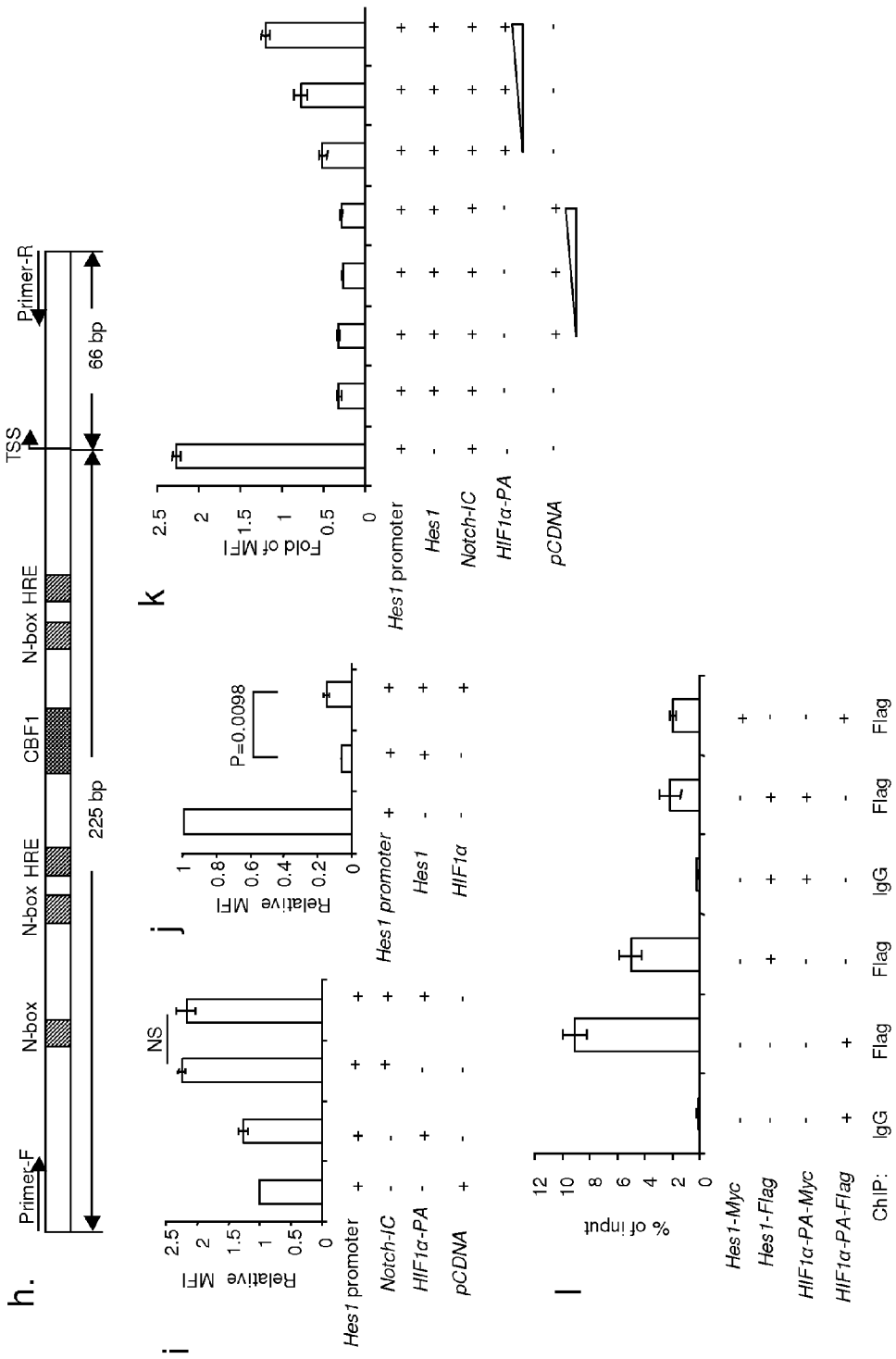
Figure 13:
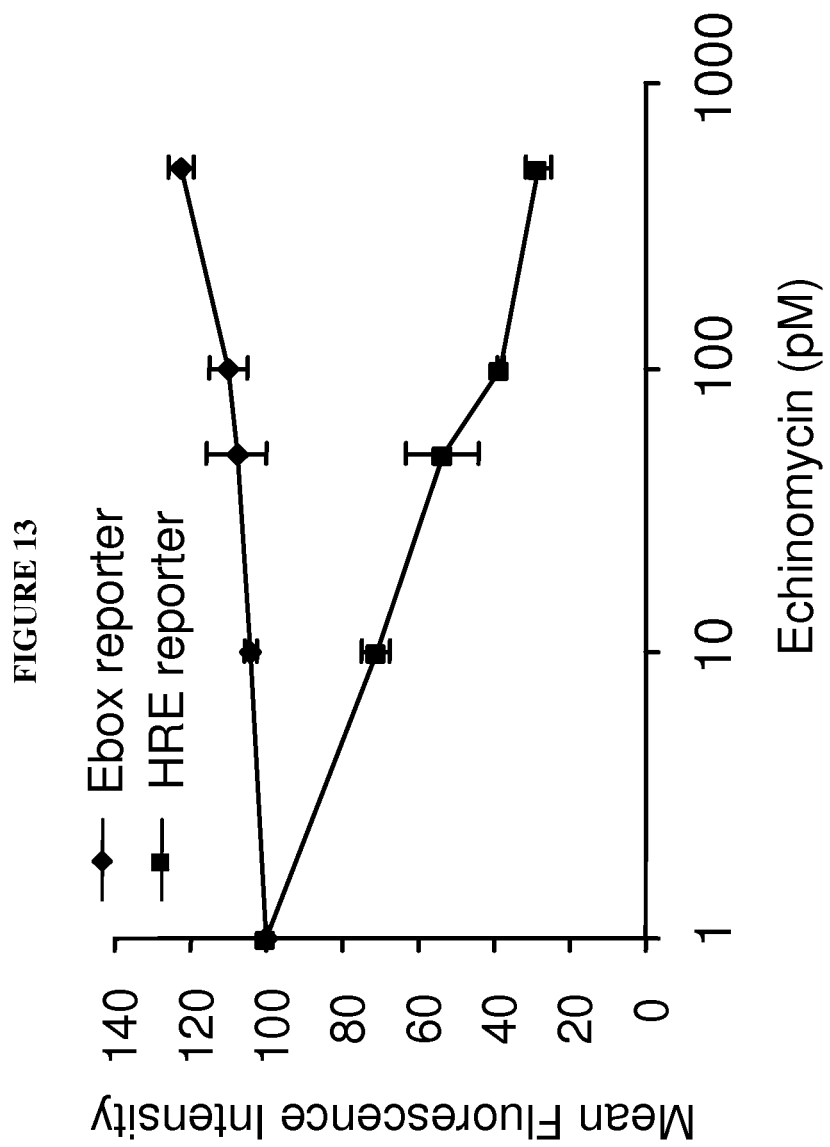
FIG. 13. At ranges used in the study, Echinomycin inhibits HIF1α but not cMyc activity. HEK293 cells were co-transfected with the Ebox or HRE reporters (see FIG. 2b) with the vector encoding c-Myc or HIF1α-PA. After 16 hours, the cells were treated with different concentrations of Echinomycin for additional 24 hrs. The transcriptional activities of c-Myc and HIF1α were quantified by flow cytometry. The untreated group is defined as 100%. Data shown are means+/−S.D. of triplicates. The experiment was repeated three times.

To test the general significance of HIF1α, we analyzed expression and function of the HIF1α in human acute myeloid leukemia (AML)-initiating cells. Leukemia-initiating cells of AML have a phenotype of CD38−CD34+. To determine whether the HIF1α gene is over-expressed in this subset, the CD38−CD34+, CD38+CD34+, CD38−CD34− and the CD38+CD34− subsets were sorted by FACS (FIG. 3d) and the expression of HIF1α and its target GLUT1 were analyzed. As shown in FIG. 3e, the CD38−CD34+ subset had the highest levels of HIF1α transcript. Correspondingly, GLUT1 transcript was also elevated in the CD38−CD34+ cells. All 6 cases of AML tested showed increased expressions of HIF1a and GLUT1 in the CD38−CD34+ subset (data not shown), which indicate that increased HIF1α expression is a general feature of those bearing markers of AML-initiating cells, The CD38⁻CD34⁺ are also known to form AML-colonies in vitro, which provides us with a simple assay to test the significance of HIF1a. As shown in FIG. 6f, for all cases tested, echinomycin inhibitions colony formation with IC50 between 50-120 pM. Although the echinomycin is also known to inhibit c-Myc activity, its IC50 is in the nM range. As shown in FIG. 13, in the ranges used in this study, echinomycin strongly inhibited HIF1α but had no effect on c-Myc function. Given the fact that the AML cases used have diverse genetic alterations (Table S2), the broad inhibition by echinomycin is consistent with an important function of HIF1α in AML-CFU, which include the CD38⁻CD34⁺ AML-initiating cells.

Example 3

Down-Regulation of Vhl in CSC is Essential for Maintenance of CSC

Since HIF1α is normally degraded under normoxia by a VHL-dependent mechanism, the expression of Vhl in the CSC was also tested. The data demonstrate an approximate 4-fold reduction in the Vhl transcripts of c-Kit⁺Sca-1⁺ cells (FIG. 5a). To determine the significant of Vhl down-regulation, the tumor cells were infected with Vhl-expressing lentivirus that also expresses GFP. The GFP$^{hi}$ and GFP$^{lo}$ subsets were compared for the abundance of the c-Kit⁺Sca-

TABLE S2

| Sample | FAB type | Age | Rx status at enrollment | Flts status exons13-15 and 20 | Cytogenetics at diagnosis |
|---|---|---|---|---|---|
| MI-AML-9 | M4 | 64 | untreated | WT | 46, XY[20][b] |
| MI-AML-15 | M4 | 58 | pre-treated | heterozygous point mutation: Y572YC in exon 14 | 46, XY[20] |
| MI-AML-32 | M0 | 55 | untreated | WT | 47, XY, +21[4]; 46, XY[16] |
| MI-AML-36 | M4 | 55 | untreated | WT | 46, XY, t(11; 19)(q23; p13.1)[20] |
| MI-AML-60 | M1 AML- | 52 | untreated | Internal tandem duplication | 46, XY[20] |
| MI-AML-71 | NOS | 73 | pre-treated | WT | 45, XX, −7[20] |

[a]Genetic analysis of the following genes were carried out and found to be of wild-type (WT): Trp53, NPM1, K-RAS and N-RAS.
[b]Numbers in bracket are the number of cells found of the same karyotypes among a total of 20 cells analyzed.

Methods

To obtain the data shown in Table S2, primers to amplify exons 5-9 of p53, exons 13-15 and exon 20 of Flt3, exon 12 of NPM1 and exons 2-3 of N-ras and K-ras were designed using the primer3 program (Steve Rozen and Helen J. Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386). PCR was used to amplify exons of interest using genomic DNA from FACS-sorted blasts as template. DNA was prepared for direct sequencing using nested sequencing primers and Exo-SAP. Mutations were identified using the Mutation Surveyor program and visual inspection of sequence tracings.

Figure 4:
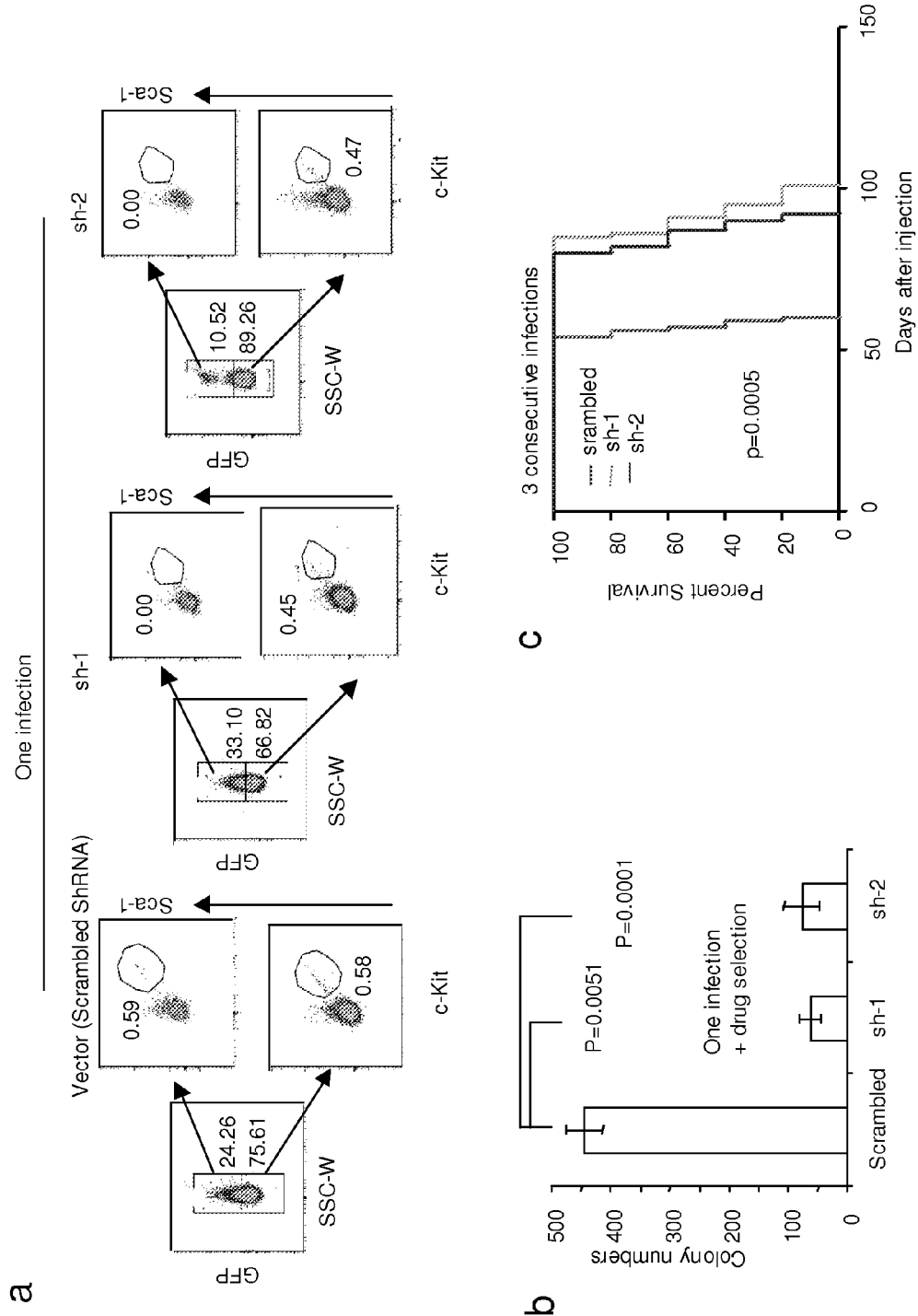
FIG. 4. ShRNA silencing revealed a critical role for HIF1α in CSC maintenance. a. Silencing HIF1α abrogates the c-Kit$^+$Sca-1$^+$ CSC. TGB tumor cells were infected with either lentiviral vector control with scrambled ShRNA (core sequence 5'-tct cgt cat aac aag ttg a-3), or lentiviral vector expressing two independent ShRNA (sh-1 or sh-2). Three days after infection, the bulk tumor cells were analyzed by flow cytometry. The GFPhi and GFPlo cells were gated and analyzed for expression of c-Kit and Sca-1. b. HIF1α shRNA reduces CFU. The cultured lymphoma cells were infected with either lentiviral HIF1α shRNA or vector with scrambled ShRNA by spinoculation, and the infected cells were selected with 5 μg/ml of blasticidin for one week. The infected cells were seeded into 1% of methylcellulose culture medium at the density of $2\times10^5$/well. The colony numbers were counted under a microscope. Data shown are means and SD of colony numbers in triplicates and are representative of three independent experiments. c. HIF1α shRNAs abrogate tumor-initiating activity. TGB tumor cells were infected 3 times with lentiviral expressing scrambled ShRNA or HIF1α ShRNA and then injected into B10.BR mice ($9\times10^5$/mouse, i.p.). The survival of the recipient mice (n=5) was compared by Kaplan-Meier analysis. All mice that succumbed have developed lymphoma as revealed by necropsy. All data in this figure have been repeated at least twice.
Figure 14:
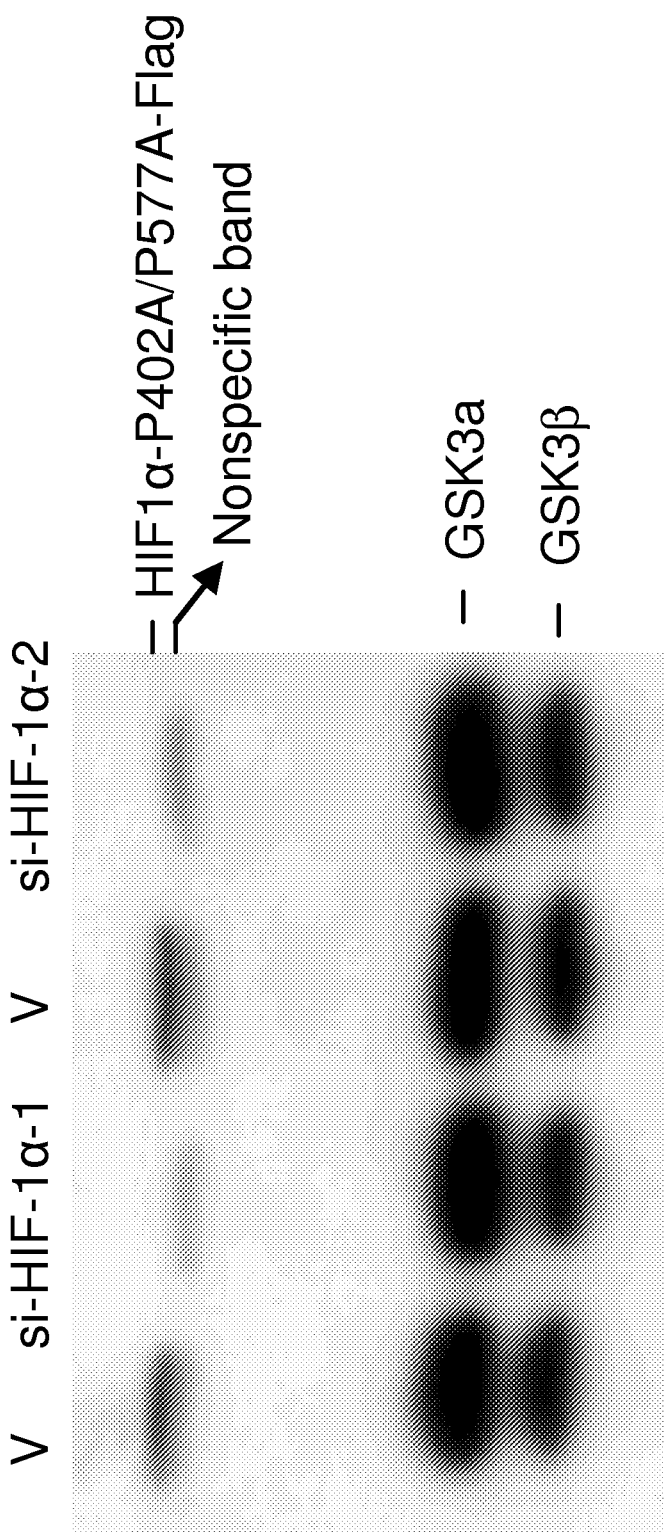
FIG. 14. Verification of the efficacy of HIF-1α shRNA. The 293T cells were transfected with a cDNA encoding the HIF-1α mutant (P402A/P577A) that is stable under normoxia condition in conjunction with either control vectors V (Core scrambled sequence: 5'-cgcgtagcgaagctca taa-3') or HIF-1α shRNA-1 and -2. The cell lysates were probed with anti-Flag mAb 24 hours after transfection.

To establish the significance of HIF1α up-regulation in the c-Kit⁺Sca-1⁺ cells, lentiviruses expressing HIF1α shRNA (see FIG. 14 for validation of shRNA) were first used to transduce the lymphoma cells. GFP was used to track cells expressing the lentiviral vector. As shown in FIG. 4a, in the vector control group with scrambled ShRNA, equal numbers of c-Kit⁺Sca-1⁺ cells were found in GFP$^{hi}$ and GFP$^{low}$ subsets. In contrast, in two shRNA-transduced tumors, the GFP$^{hi}$ population were essentially devoid of the c-Kit⁺Sca-1⁺ cells, which indicated that the silencing of HIF1α abrogates the c-Kit⁺Sca-1⁺ subset. Since more than 50-fold reduction of CSC was observed on day 3 after transduction, HIF activity is required for the maintenance of the c-Kit⁺Sca-1⁺ CSC.

Consistent with this notion, after drug selection to enrich the transduced cells, the colony formation assay revealed 70-80% reduction in the HIF1α ShRNA-transduced cells (FIG. 4b). To test the role for HIF1α in tumor-initiating activity, control vector (with scrambled shRNA) or HIF1α shRNA-transduced tumor cells were transplanted into B10.BR mice after three rounds of transduction. As shown in FIG. 4c, transduction with either shRNA significantly reduced tumor-initiating activity as judged by the significant delay of tumor-related death.

Figure 5:
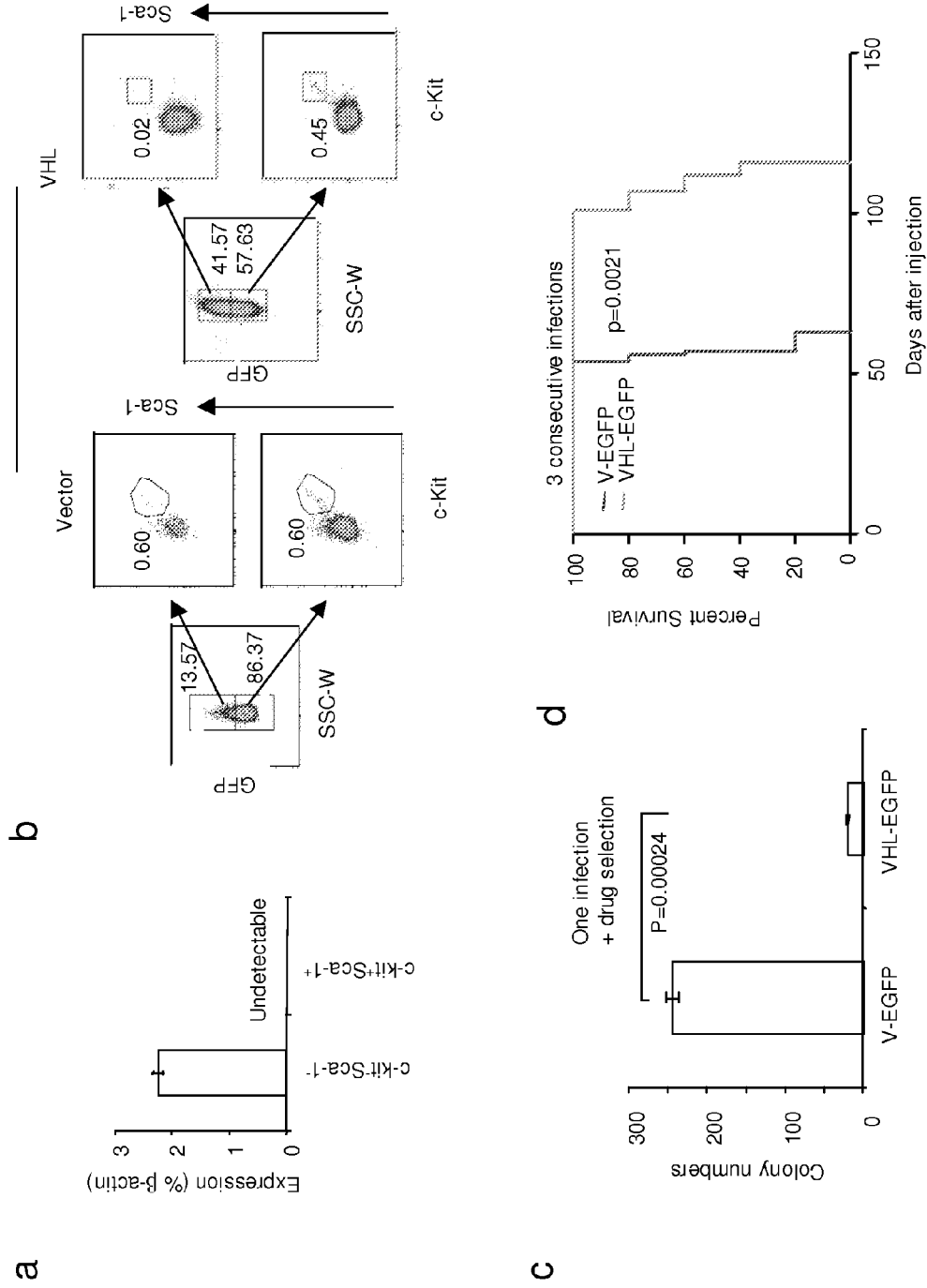
FIG. 5. Down-regulation of the Vhl gene is essential for maintenance of CSC. a. Down-regulation of Vhl transcript in c-Kit$^+$Sca-1$^+$ cells. TGB thymoma cells were sorted into c-Kit+Sca-1+ and c-Kit$^-$Sca-1$^-$ subsets, as described in FIG. 1, the levels of Vhl transcripts were determined by real-time PCR. b. Ectopic expression of Vhl ablated CSC. TGB tumor cells were infected with either lentiviral vector control, or lentiviral vector expressing two Vhl cDNA. Three days after infection, the bulk tumor cells were analyzed by flow cytometry. The GFPhi and GFPlo cells were gated and analyzed for expression of c-Kit and Sca-1. c. Vhl expression reduces tumor CFU. The cultured lymphoma cells were infected with either lentiviral Vhl cDNA or vector by spinoculation, and the infected cells were selected with 5 μg/ml of blasticidin for one week. The transduced cells were seeded into 1% of methylcellulose culture medium at a density of $2\times10^5$/well. The colony numbers were counted under a microscope. Data shown are means and SD of colony numbers in triplicates and are representative of three independent experiments. d. Ectopic expression of Vhl cDNA inhibits tumor-initiating activity. TGB tumor cells were infected 3 times with lentiviral expressing vector alone or HIF1α ShRNA and then injected into B10.BR mice ($9\times10^5$/mouse, i.p.). The survival of the recipient mice (n=5) was compared by Kaplan-Meier analysis. The development of lymphoma was confirmed by necropsy of the succumbed mice. This experiment has been repeated twice.

1⁺ subset. The GFP$^{hi}$ subset contained no c-Kit⁺Sca-1⁺ cells (FIG. 5b). Thus, high Vhl expression ablated the c-Kit⁺Sca-1⁺ cells. Consistent with this, the ectopic expression of Vhl significantly reduced the colony forming activity of the tumor cells (FIG. 5c). To test the role for reduced Vhl in tumor-initiating activity, vector and VHL cDNA transduced tumor cells were transplanted into B10.BR mice. As shown in FIG. 5d, transduction with lentivirus expressing Vhl cDNA significantly reduced tumor-initiating activity as judged by the onset of tumor-related death of the recipients. Taken together, the data presented in FIGS. 4 and 5 demonstrate that both over-expression of HIF1α and reduction in VHL are essential for CSC activity.

Example 4

HIF Acts in Concert with the Notch Pathway in Self-Renewal of CSC

In order to determine the underlying molecular mechanisms by which HIF1α activation promotes self-renewal of CSC, the potential involvement of Wnt and Notch pathways was examined. Despite activation of the Wnt signaling in the TGB tumor, the data demonstrate that the dominant negative TCF-1, which was shown to inhibit tumor growth associated with Epm2a down regulation, did not affect the CFU of the TGB CSC (data not shown). In contrast, g-secretase inhibitor, L-685, 458, an inhibitor for Notch, potently blocked the colony forming activity (FIG. 6a). To determine whether the Notch signaling is over-activated in the CSC, the c-Kit⁺Sca-1⁺ cells were sorted and compared with the bulk c-Kit⁻Sca-1⁻ cells for expression of the Notch target gene Hes1. As shown in FIG. 6b, sorted CSC had approximately 3.5 fold increase in expression of Hes1. In order to test whether the increased Notch activity depended on HIF activity, three different HIF inhibitors were used to block the up-regulation of Notch targets in total TGB lymphoma cells and CSC enriched for c-Kit+ cells. The data in FIG. 6c demonstrated that all HIF inhibitors blocked expression of Hes1 among the c-Kit+ CSC.

Figure 15:
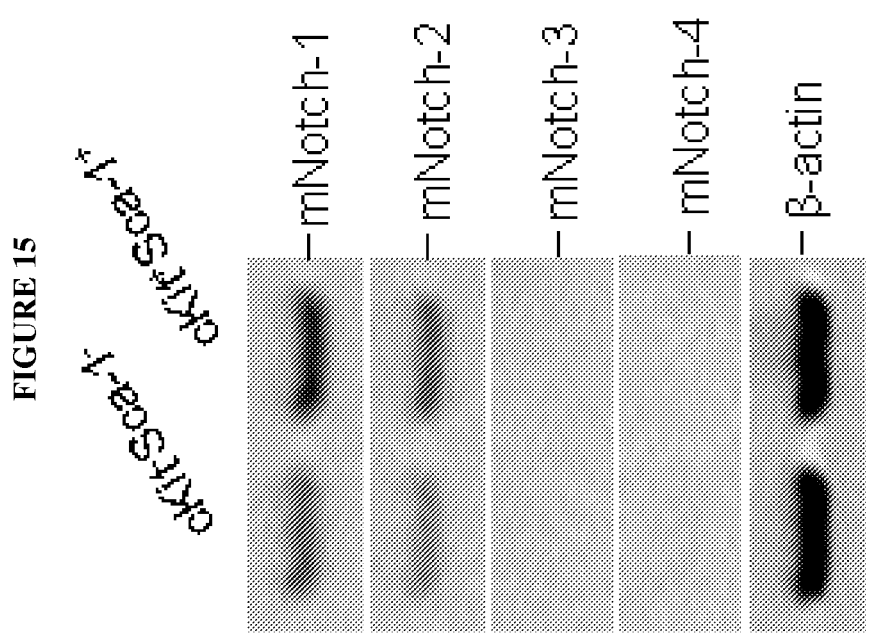
FIG. 15. TGB tumor cells express both Notch 1 and Notch 2. The TGB tumor cells were sorted into c-Kit+Sca-1+ and c-Kit-Sca-1− subsets. The expression of Notch family members were detected by RT-PCR.

Expression of Notch1-4 was analyzed in c-Kit$^+$Sca-1$^+$ and the c-Kit$^-$Sca-1$^-$ tumor cells. As shown in FIG. 15, Notch1 and 2, but not Notch 3 and 4 are expressed in the TGB tumor cells. Since two Notch genes are expressed, a search for an effective dominant negative mutant to suppress Notch signaling was performed. By trial and error, a potent dominant negative mutant of Notch (AA1955-2370) was identified, comprising intracellular domains of Notch1 with truncation in both N and C-termini. A nuclear localization sequence (NLS) from SV40 virus was inserted in the N-terminus to facilitate its translocation into the nuclei. Based on the structure of Notch I-C/CSL/Mastermind/DNA complex, the deletion removed both the DNA binding RAM domain and the 4 ankyrin repeats responsible for binding N-terminus of mastermind, while returning the bulk of CSL-interacting residues. As such, it is predicted to act as a dominant negative regulator of Notch signaling by preventing the formation of mastermind-CSL-Notch IC-DNA complex. The mutant was called dRdA$_{1-4}$dOP (FIG. 6d, left panel). As shown in FIG. 6d right panel, transduction of the dominant mutant resulted in about 30-fold reduction of the Hes transcripts. To substantiate the role for Notch signaling, the TGB lymphoma was transduced with either control lentiviral vector or that expressing dRdA$_{1-4}$dOP. The transduced cells were marked with GFP. As shown in FIG. 6e, in the vector control group, the % of c-Kit$^+$Sca-1$^+$ cells were comparable among the GFP$^{hi}$ and GFP$^{lo}$ cells. In contrast, dRdA$_{1-4}$dOP-transduced group, more than 5-fold reduction in the % c-Kit$^+$Sca-1$^+$ cells was observed in the GFP$^{hi}$ subset. These data demonstrate that inactivation of the Notch pathway prevents the survival of the c-Kit$^+$Sca-1$^-$ cells. In serial plating experiments, transduction of dRdA$_{1-4}$dOP reduced self-renewal activity as revealed by colony formation assay (FIG. 6f). Moreover, when the dRdA$_{1-4}$dOP- or control vector-transduced cells were transplanted into syngeneic mice, it was clear that dRdA$_{1-4}$dOP-transduction prevented the development of lymphoma, as demonstrated by the survival analysis (FIG. 6g).

Previous studies demonstrated that HIF1α may interact with Notch directly to activate its target gene, Hey2, under hypoxia conditions. Using the reporter for Hes1 promote activity, however, no significant enhancement of Notch signaling by the oxygen-resistant HIF1α mutant was observed (FIGS. 6h, i). Alternative explanations for the function of HIF1α in Hes1 expression was therefore explored. It is well established that, in response to Notch signaling, Hes1 expression is self-limiting, and that the negative feedback is mediated by Hes1 binding to the N-boxes in the Hes1 promoter region. Interestingly, immediately after each of the two critical N-boxes, a bona fide HRE was identified (FIG. 6h and FIG. 16). Given their proximity, it was hypothesized that HIF1α may directly inhibit autoregulation of Hes1. Indeed, transfection of Hes1 cDNA reduced the Hes1 promoter activity by about 10-fold. This inhibition was partially reversed by the oxygen-resistant HIF1α (FIG. 6j). Likewise, in the presence of Notch IC cDNA, Hes1 also repressed its own promoter. HIF1α reversed the repression in a dose dependent manner (FIG. 6k). Using chromatin immunoprecipitation (FIG. 6l), significant binding of HIF1α to the region bound by Hes1 was observed. Interestingly, the binding HIF1α and Hes1 appear to compete with each other in binding to the region. The data suggest that HIF1α may enhance Notch-induced Hes1 expression by antagonizing the autoregulation of the Hes1.

Example 5

A Role for HIF in CSC Maintenance

The re-emergence of CSC concept relied on transplantation studies to identify a subset of self-renewing tumor initiating cells. Since most studies involved xenogeneic and allogeneic transplantation into immune-deficient host, some have suggested that the CSC concept requires reappraisal. An important feature of the current study is to use syngeneic immune competent mice as recipients. The self-renewing capacity of the CSC identified in this study has been demonstrated by three rounds of serial transplantation, in which as few as 100 c-Kit$^+$Sca-1$^+$ cells can give rise to lymphoma in nearly 100% of the recipients. During the process, the number of c-Kit$^+$Sca-1$^+$ cells remains around 1%. While maintaining the expression of the CD8 co-receptor, the bulk lymphoma cells appear to gradually lose the expression of the T cell receptor. In addition to giving rise to lymphoma, almost all c-Kit$^+$Sca-1$^+$ cells exhibit CFU activity. The data substantiate an increasing list of genetic studies in supporting the notion of CSC, although the potential variation in tumor models with regard to existence of CSC cannot be ruled out.

Both in vitro self-renewal and in vivo tumor initiating properties were used to characterize the molecular mechanism of self-renewal of CSC. In both assays, the role for HIF1α was demonstrated by drug inhibition, shRNA silencing and over-expression of oxygen-dependent HIF inhibitor VHL. Since the expression of transduced vectors leads to almost immediate disappearance of the CSC population, and since the short-term treatment (12 hours) of echinomycin resulted in a specific reduction of the c-Kit$^+$Sca-1$^+$ cells by increased apoptosis, the HIF1α is likely necessary for survival of CSC.

The increased HIF activity in the murine lymphoma is caused by both over-expression of HIF1α and down-regulation of Vhl. Since Vhl is responsible for the oxygen-mediated degradation of HIFα, the increased HIFα activity no longer requires hypoxic environment. In addition, it should be noted that in the 6 cases AML samples tested, we have not observed increased expression of VHL (data not shown). Yet the HIF are active based on expression of its target and sensitivity to echinomycin. Therefore, additional mechanisms likely exist to allow oxygen-resistant function of HIF in AML-CFU. The effect of low doses of echinomycin on all AML samples tested suggest that the mechanism described herein may be generally applicable for tumors grown in area with high levels of blood supplies, including leukemia and lymphoma. For areas of solid tumors with poor blood supplies, the mechanism can be operative even without HIF over-expression or VHL down-regulation.

Example 6

A Molecular Pathway for Maintenance of CSC

In investigating the molecular pathway responsible for the maintenance of CSC, enhanced activity of Notch pathway was observed, as revealed by increased expression of Notch target genes, in the CSC in comparison to the bulk tumor cells. The data demonstrate that all three HIF inhibitors tested block Notch activation in the c-Kit$^+$ subset. Interestingly, the inhibition appear specific for the c-Kit$^+$ subset of TGB lymphoma, which is enriched for CSC, as the drugs had no effect on the Notch target expression if the total TGB lymphoma cells were used. The significance of Notch in CSC maintenance and tumor development is demonstrated by effective ablation of the CSC and tumorigenesis by an ectopic expression of a dominant inhibitor of Notch signaling, dRdA$_{1-4}$dOP in the TGB tumor cells. Again, the selective ablation demonstrates that Notch signaling is specifically required for the maintenance of CSC, while the survival of the bulk tumor cells is independent of Notch signaling. Taken together, these data demonstrate that HIF maintains CSC by regulating Notch signaling.

Hes1 is an important Notch target known to be critical for stem/progenitor cell functions. The data described herein indicate that HIF1α potentiated the induction of Hes1 by Notch. In contrast with the previous studies using Hey2 promoter as readout, no direct co-operation between HIF1α and Notch IC in the induction of the Hes1 gene was observed. Rather, it was shown that HIF1α prevents the negative-feedback auto-regulation of the Hes1 gene by inhibiting its binding to the N-boxes in the Hes1 promoter. Given the general, although not necessarily universal, role of Notch in maintenance of a variety of tissue stem cells, the data indicate an important functional conservation between CSC and tissue stem cells.

Example 7

The HIF Pathway Plays a Role in CSC Function

Figure 17:
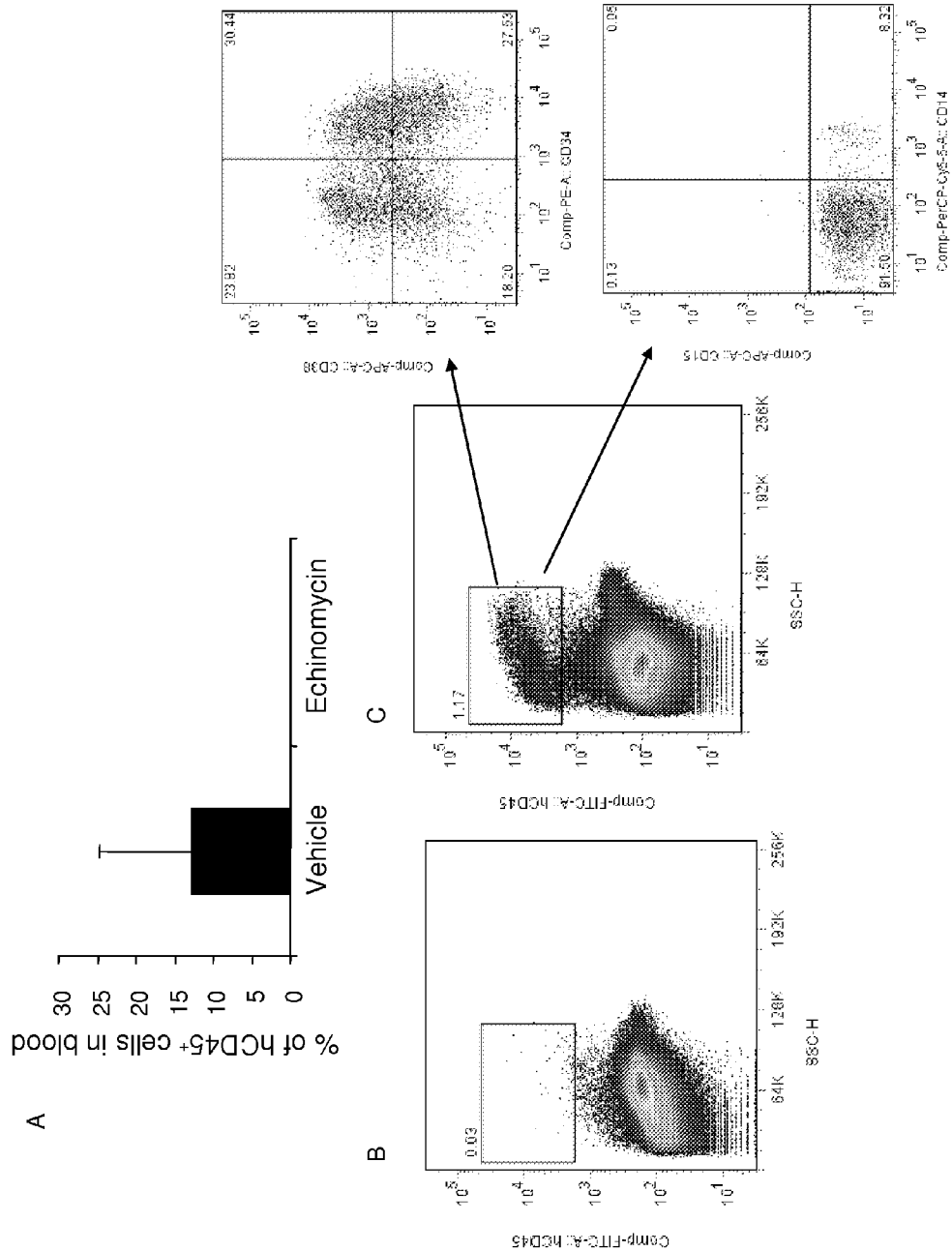
FIG. 17. Echinomycin abrogated AML in NOD-SCID mice. A. Elimination of AML-derived human cells in the blood of recipient mice. Data shown are means and S.D. (n=3). B. Lack of human cells in echinomycin-treated mice. Data shown are representative profile of human CD45 expression among bone marrow cells. Essentially identical profiles were obtained with two other mice. B. Human AML cells in the bone marrow of untreated mice. The left panel shows human CD45 staining of bone marrow cells, while the right panels show phenotypes of the gated human CD45+ cells. Data shown are representative of three mice per group.

An important way to validate the role for HIF pathway in the CSC function was to test whether HIF inhibitor echinomycin can be used to treat AML in a xenogeneic model. Studies using two AML samples have been performed. 6×10$^6$ AML cells (either AML71-PB, which had poor prognosis based on cytogenetics data, or AML-15-PB which had moderate prognosis based on cytogenetics; see Table S2 above) from blood were transplanted into sublethally irradiated NOD-SCID mice. Starting at 2 weeks after transfer, half of the recipient mice received three injections of 200 ng/mouse/injection of echinomycin, once every other day. After two weeks of pause, these mice received 3 more injections. The other half of the mice were left untreated as control. At 7 weeks after transplantation, all untreated mice in both groups (3 mice per group) became moribund, while all echinomycin treated mice were healthy. Analysis of the peripheral blood and bone marrow of AML-71PB recipients is shown provided in FIG. 17.

As shown in FIG. 17A, the untreated group had an average of 12% human CD45$^+$ cells in the blood. Echinomycin treatment completely wiped out human CD45$^+$ cells. A clearly definable human cell population was observed in the bone marrow of untreated bone marrow, but not with the echinomycin treatment (FIGS. 17B and C). Further analysis of the human CD45$^+$ cells indicated that they were immature, as judged by their lack of CD14 and CD15 marker (FIG. 17C lower right panel). Moreover, a high proportion of the human CD45$^+$ cells exhibited marker of AML stem cells (CD34$^+$CD38$^-$), as indicated in FIG. 17C (upper right panel). These data demonstrated the feasibility of the xenogeneic model and critical support for treating hematologic cancer such as AML using echinomycin. These data help demonstrate that HIF1α activity is required for the maintenance of stem cells for hematological malignancies and that HIF serves as a valuable therapeutic target for cancer therapy. More importantly, the data establish that the same principle applies to human AML.

Example 8

Therapeutic Elimination of Leukemia Stem Cells for AML

Figure 18:
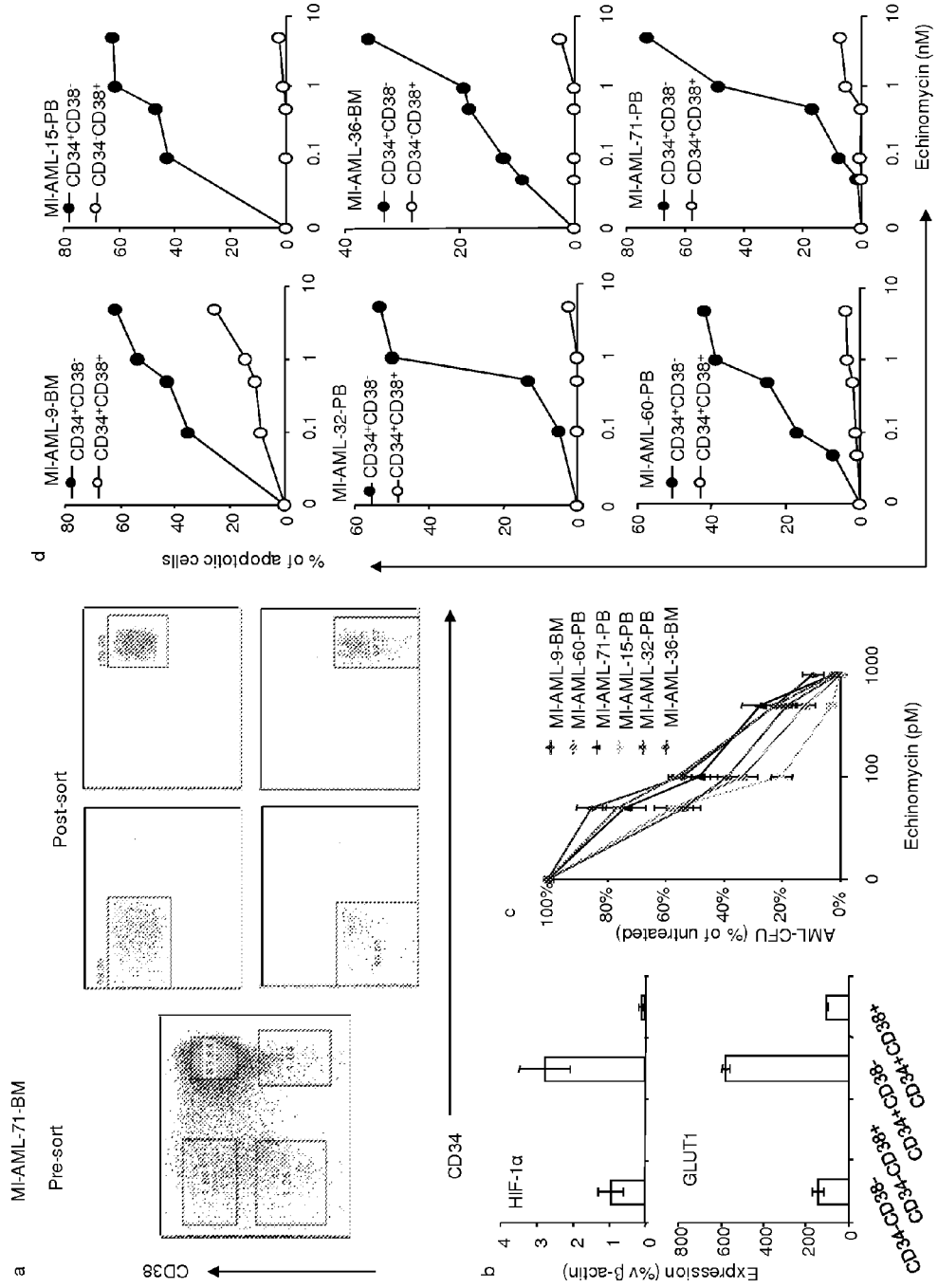
FIG. 18. HIF1α is a target for therapeutic elimination of human AML in a xenogenic mouse model. a. Isolation of 4 subsets of tumor cells in AML samples. Bone marrow cells from AML patient MI-AML-71 were stained for CD34 and CD38 and sorted into 4 subsets for RNA isolation. The presort samples and the gates used for sorting are shown in the left panel and the post-sorted populations are shown in the middle and right panels. The percentages of cells in each gate are provided in the panels. b. Expression of HIF1α (top) and GLUT1 in the subsets. Data shown are means+/−S.D. of transcript levels of the genes, presented as % of β-actin from the same samples. Enhanced expression in the CD34+CD38− samples was observed in all 6 AML samples tested. c. AML-CFU in all 6 AML samples were highly sensitive to echinomycin. AML samples ($2.5 \times 10^5$/ml) from either peripheral blood (PB) or bone marrow (BM) were pretreated with given concentrations of echinomycin in 2 ml medium for 24 hours. Treated viable cells were then plated at $10^5$/well for CFU assay in triplicates. The colony numbers were counted 7-10 days later. The data shown are % means+/−S.D. of untreated controls. d. Echinomycin selectively eliminates the CD34+CD38− subset of AML cells. Primary AML samples were cultured with given doses of echinomycin or vehicle control for 30 hours in RPMI 1640 containing 10% fetal calf serum and human cytokine cocktail consisting of CSF, GM-CSF and IL-3 at a density of $5 \times 10^5$/ml. The cells were stained with antibodies against CD34, CD38 in conjunction with Annexin V and DAPI. Data shown are the % of Annexin V+DAPI−/+ cells. The Annexin V+ cells % in vehicle treated group was subtracted. The filled symbols show the data for the CD34+CD38− subsets, while the open symbols show data for the bulk leukemia cells (CD34+CD38+ for AML9, AML32, AML60 and AML71 and CD34−CD38+ for AML15 and AML36). These data were repeated twice. e-h. Therapeutic effect of echinomycin. e. Therapeutic effect of human AML in NOD-SCID mice, data shown are % of human CD45 (hCD45)+ cells in the bone marrow of the recipient mice at 40 days after last treatment. The therapeutic effect has been repeated twice. f. Echinomycin does not induce differentiation of AML cells in vivo, as revealed by lack of mature myeloid markers on the bulk of human cells in treated and untreated group. Data shown are profiles of CD14 and CD15 among human CD45+ cells. g. Selective depletion of the CD34+CD38− subset by echinomycin. Data shown in the top panels are the abundance of CD34+CD38− subsets in mouse bone marrow, while the lower panel shows that within human leukemia cells. h. Despite presence of leukemia cells, bone marrow from echinomycin-treated mice failed to reinitiate leukemia in the new NOD-SCID mice. Representative profiles are presented in the top panel, while the summary data from 5 mice per group are presented in the lower panel.
Figure 18:
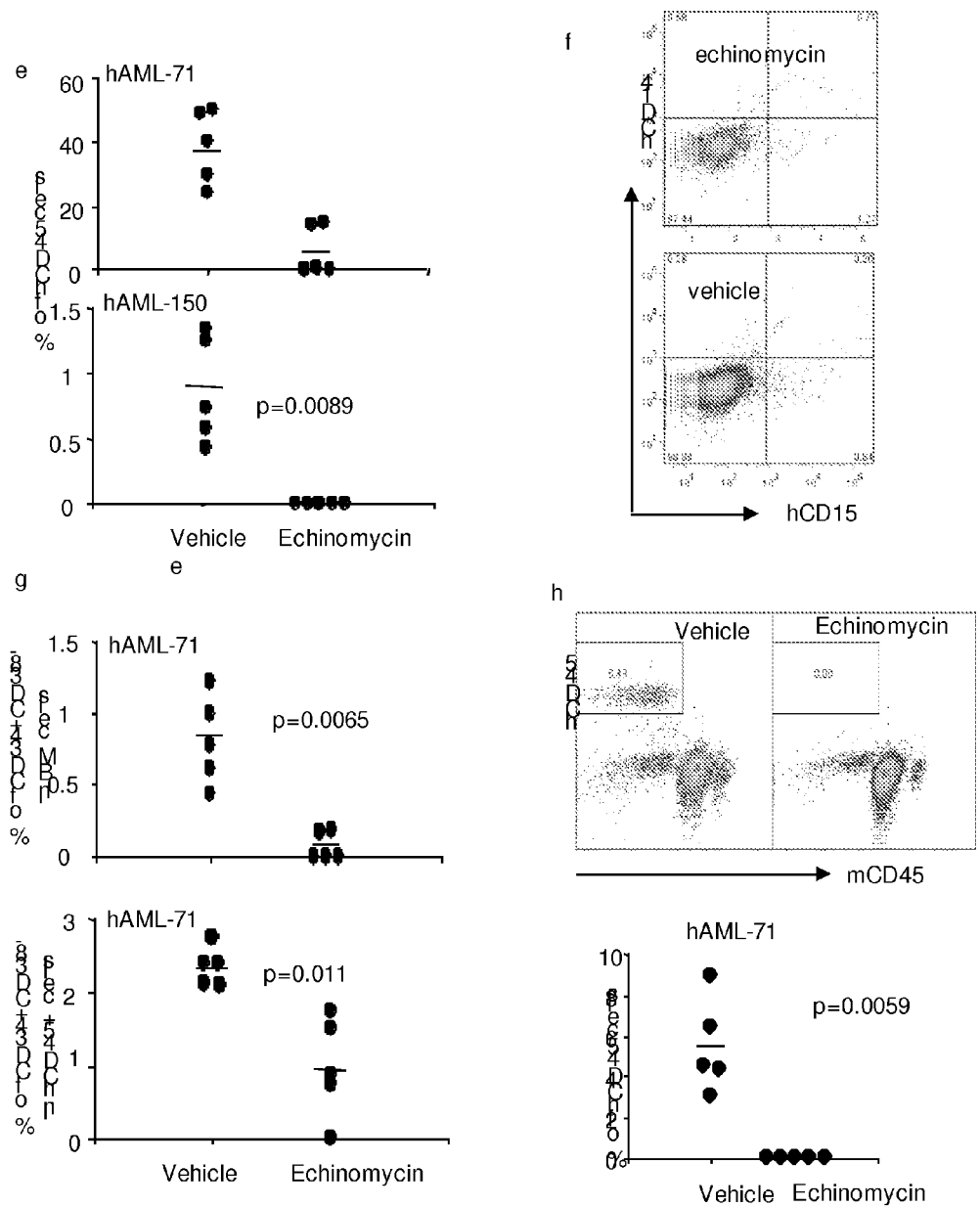

This example demonstrates the therapeutic potential of HIF inhibitors for human hematological malignancies. AML was used as a model because the phenotype of AML leukemia stem cells (AML-LSC) was well-characterized, and because AML-LSC function in vivo can be assayed using an established xenogeneic model. AML-LSC have the phenotype of CD34$^+$CD38$^-$. To determine whether the HIF1α gene is over-expressed in this subset of cells, CD34$^+$CD38$^-$, CD34$^+$CD38$^+$, CD34$^-$CD38$^-$ and CD34$^-$CD38$^+$ subsets were sorted by FACS (FIG. 18a), and the expression of HIF1α and its target GLUT1 were analyzed. As shown in FIG. 18b, the CD34$^+$CD38$^-$ subset had the highest levels of HIF1α transcript. Correspondingly, GLUT1 transcript was also elevated in the CD38$^-$CD34$^-$ cells. All 6 cases of AML tested showed increased expressions of HIF1α and GLUT1 in the CD38$^-$CD34$^-$ subset (data not shown), which indicate that increased HIF1α expression is a general feature of those cells bearing markers of AML-LSC cells.

CD34$^-$CD38$^-$ cells are also known to form AML-colonies in vitro, thereby providing a simple assay to test the significance of HIF1α. As shown in FIG. 18c, for all cases tested, echinomycin inhibited colony formation with an IC50 between 50-120 pM. Although the echinomycin is also known to inhibit c-Myc activity, its IC50 for c-Myc is in the nM range. The broad inhibition by echinomycin is consistent with an important function of HIF1α in AML-CFU, which include the CD34$^+$CD38$^-$ AML-LSC.

Conventional cancer therapy appears to enrich cancer stem cells. An NFkB inhibitor, dimethylamino analog of parthenolide, showed some selectivity for AML-LSC. Since the HIF1α activity appears to be selectively activated in AML, AML-LSC might be selectively targeted by echinomycin. As shown in FIG. 18d, low doses of echinomycin selectively induced apoptosis of the CD34$^+$CD38$^-$ population, in comparison to the dominant AML cells (CD34$^+$CD38$^+$ for most but CD34$^-$CD38$^+$ for two AML cases).

A xenogeneic AML model using human AML samples was established to test whether echinomycin can be used as a potential therapeutic agent for AML. Primary clinical samples from AML patients reconstituted irradiated NOD-SCID mice with immature human myeloid cells were characterized by the expression of human CD45, CD11b, but not mature myeloid markers CD14 and CD15. Remarkably, a short term treatment with echinomycin starting at 15 days after transplantation completely eliminated human cells from sample AML 150 and dramatically reduced the burden of human leukemia of AML 71 (FIG. 18e). The residual cells in echinomycin treated mice were not differentiated as judged by the lack of mature myeloid markers CD14, and CD15 (FIG. 18f).

The incomplete remission of AML71 enabled a determination of whether echinomycin selectively reduces the AML-LSC, using the CD34$^+$CD38$^-$ markers. Echinomycin reduced the percentage of CD34$^+$CD38$^-$ cells in bone marrow by more than 10-fold (FIG. 18g, top panel). Even among the human CD45$^+$ compartment, the relative abundance of AML-LSC was also reduced (FIG. 18g, lower panel). To substantiate the impact of echinomycin on the leukemia initiating cells, serial transplantation studies were carried to determine whether echinomycin reduced self-renewal of AML-LSC. As shown in FIG. 18h, while bone marrow from untreated mice induced leukemia in all new recipients, bone marrow from echinomycin treated mice failed to do so in any recipients. Therefore, the residual cells in the echinomycin-treated bone marrow were devoid of AML-LSC.

Example 9

Experimental Procedures

Materials and Methods for Examples 1-7 are disclosed below.

AML Samples

AML patients diagnosed at the University of Michigan Comprehensive Cancer Center between 2005 and 2009 were enrolled into this study. The study was approved by the University of Michigan Institutional Review Board. Written informed consent was obtained from all patients prior to enrollment. The same AML diagnostic criteria (>=20% myeloblasts in the bone marrow or peripheral blood) were used and determined FAB subclassification through review of both laboratory and pathology reports dated at the time of diagnosis and interpreted by hematopathologists. Cytogenetic risk stratification was determined according to SWOG/ECOG criteria.

Antibodies, Flow Cytometry, and Immunofluorescence

Fluorochrome-conjugated antibodies specific for CD117 (c-kit) and Ly-6A/E (Sca-1) were purchased from either e-Bioscience (Ja Jolla, Calif.), while those specific for CD8 and Vβ8 were purchased from Becton Dickinson-Pharmingen (Ja Jalla, Calif.). The cell surface markers were analyzed by flow cytometry using LSRII (Becton Dickinson, Mountain View, Calif.). The specific subsets were sorted by FACSAria.

RT-PCR and Real-Time PCR

Expression of HIF1α, HIF-2α, HIF-3α, VHL, and Glut1 was determined by RT-PCR and real-time PCR. The primers used were HIF1α, forward, 5'-agtctagagatgcagcaagatctc-3'; reverse, 5'-tcatatcgaggctgtgtcgactga-3' (PCR), 5'-ttcctcatggt-cacatggatgagt-3' (real-time PCR); hif-2a, forward, 5'-cga-caatgacagctgacaaggag-3'; reverse, 5'-ttggtgaccgtgcacttcatc-ctc-3'; hif-3a, forward, 5'-atggactgggaccaagacaggtc-3'; reverse, 5'-agcttcttctttgacaggttcggc-3'; vhl, forward, 5'-tctca-ggtcatcttctgcaac-3'; reverse, 5'-aggctccgcacaacctgaag-3'; Glut1, forward 5'-tgtgctgtgctcatgaccatc-3' and reverse 5'-ac-gaggagcaccgtgaagat-3'; mHes1F: gccagtgtc aacacgacaccgg, mHes1R: tcacctcgttcatgcactcg; HIF1αF, 5'-ccatgtgaccatgag-gaaatgagag-3'; HIF1αR, 5'-tcatatccaggctgtgtcgactgag-3'; GLUT1F, 5'-tcaatgctgatgatgaacctgct-3'; GLUT1R, 5'-ggt-gacacttcacccacataca-3'.

ShRNA-Mediated Knockdown of HIF1α and Ectopic Expression of VHL and dRdA1, 2dOP

Lentiviral vectors carrying siRNAs are known in the art. The core sequence of HIF1α-ShRNA-1 is 5'-ctagagatgcag-caagatc-3', while that of HIF1α-ShRNA-2 is 5'-gagagaaat-gcttacacac-3'. The same vector was used to express full length VHL cDNA, and dominant negative Notch mutant dRdA1-42dOP (AA1995-2370). The tumor cell cultures were infected with either control lentivirus or lentivirus encoding HIF1α shRNA, dRdA1-42dOP or VHL cDNA by spinoculation. The cultures were selected with 5 µg/ml of blasticidin for 5 days to remove uninfected cells.

In vitro colony formation assay for tumor cells and bone marrow cells is known in the art.

In Vivo Tumorigenicity Assay

Given numbers of total tumor cells or sorted subsets were injected into either immune competent B10.BR mice or RAG-2$^{-/-}$BALB/c mice. Moribund mice were considered to have reached experimental endpoint and were euthanized. The therapeutic effects were analyzed by Kaplan Meier survival analysis.

The invention claimed is:

1. A method of reducing self-renewal of acute myeloid leukemia (AML) cancer stem cells in a subject with post-remission AML, without adverse effect on hematopoietic stem cells (HSCs),
   wherein said method consists of administering echinomycin and a pharmaceutically acceptable carrier to a subject in need thereof, and
   wherein said administration results in a serum concentration of echinomycin ranging from 0.01 nM to 5 nM.

2. The method of claim 1, wherein the mammal carries leukemia cells of the phenotype CD38$^-$CD34$^+$.

3. The method of claim 1, wherein the serum concentration ranges from 0.1 nM to 5 nM.

* * * * *